United States Patent [19]
deSolms et al.

[11] Patent Number: 5,536,750
[45] Date of Patent: Jul. 16, 1996

[54] INHIBITORS OF FARNESYL-PROTEIN TRANSFERASE

[75] Inventors: S. Jane deSolms, Norristown; Samuel L. Graham, Schwenksville, both of Pa.

[73] Assignee: Merck & Co., Inc., Rahway, N.J.

[21] Appl. No.: 346,701

[22] Filed: Nov. 30, 1994

Related U.S. Application Data

[60] Continuation-in-part of Ser. No. 236,903, Apr. 29, 1994, which is a division of Ser. No. 968,106, Oct. 29, 1992, Pat. No. 5,326,773.

[51] Int. Cl.$^6$ .......................... A61K 31/24; A61K 31/195
[52] U.S. Cl. .......................... 514/538; 514/18; 514/562; 560/10; 560/128; 530/331; 562/444; 562/556; 562/557
[58] Field of Search .................. 530/331; 560/10, 560/128; 562/444, 556, 557; 514/18, 538, 562

[56] References Cited

U.S. PATENT DOCUMENTS

| | | | |
|---|---|---|---|
| 5,043,268 | 8/1991 | Stock | 435/15 |
| 5,141,851 | 8/1992 | Brown et al. | 435/15 |
| 5,238,922 | 8/1993 | Graham et al. | 514/18 |
| 5,326,773 | 7/1994 | De Solms et al. | 514/336 |
| 5,340,828 | 8/1994 | Graham et al. | 514/357 |
| 5,352,705 | 10/1994 | Deana et al. | 514/630 |
| 5,362,906 | 11/1994 | Anthony et al. | 562/23 |

FOREIGN PATENT DOCUMENTS

| | | |
|---|---|---|
| 0456180A1 | 11/1991 | European Pat. Off. |
| 0461869A2 | 12/1991 | European Pat. Off. |
| 0618221A2 | 10/1994 | European Pat. Off. |
| WO91/16340 | 10/1991 | WIPO |
| WO94/26723 | 11/1994 | WIPO |
| WO94/28720 | 12/1994 | WIPO |

OTHER PUBLICATIONS

Garcia, A. M., et al., "Peptidomimetic Inhibitors of Ras Farnesylation and Function in Whole Cells," Jour. of Biol. Chem., vol. 268, No. 25, pp. 18415–18418 (1993).

Spatola, A. F., "Peptide Backbone Modifications: A Structure–Activity Analysis of Peptides . . . ," Chem. and Biochem of Amino Acids, Peptides and Proteins, Ed. B. Weinstein, Pub. by Marcel Dekker, N.Y. pp. 267–357 (1983).

Gibbs, J. B. et al., "Selective Inhibition of Farnesyl–Protein Transferase Block Ras Processing in Vivo", The Journal of Biological Chemistry, vol. 268, No. 11, pp. 7617–7620 (1993).

Goldstein, J. L. et al., "Nonfarnesylated Tetrapeptide Inhibitors of Protein Farnesyltransferase", The Journal of Biological Chemistry, vol. 266, No. 24 pp. 15575–15578 (1991).

James, G. L. et al., "Benzodiazepine Peptidomimetic BZA–5B Interrupts the MAP Kinase Activation Pathway in H–Ras–transformed Rat–1 Cells, but Not in Untransformed Cells", The Journal of Biological Chemistry, vol. 369, No. 44, pp. 27705–27714 (1994).

James, G. L. et al., "Benzodiazepine Peptidomimetics: Potent Inhibitors of Ras Farnesylation in Animal Cells", Science, vol. 260, pp. 1937–1942 (1993).

Kohl, N. E. et al., "Selective Inhibition of ras–Dependent Transformation by a Farnesyltransferase Inhibitor", Science, vol. 260, pp. 1934–1937 (1993).

Kohl, N. E., "Protein farnesyltransferase inhibitors block the growth of ras–dependent tumors in nude mice", Proc. Natl. Acad. Sci. USA, Med. Sciences, vol. 91, pp. 9141–9145 (1994).

Pompliano, D. L., "Steady–State Kinetic Mechanism of Ras Farnesyl:Protein Transferase", Biochemistry, vol. 31, pp. 3800–3807 (1992).

*Primary Examiner*—C. Warren Ivy
*Assistant Examiner*—Amelia Owens
*Attorney, Agent, or Firm*—David A. Muthard; Mark R. Daniel

[57] ABSTRACT

The present invention is directed to compounds which inhibit farnesyl-protein transferase (FTase) and the farnesylation of the oncogene protein Ras. The invention is further directed to chemotherapeutic compositions containing the compounds of this invention and methods for inhibiting farnesyl-protein transferase and the farnesylation of the oncogene protein Ras.

17 Claims, No Drawings

INHIBITORS OF FARNESYL-PROTEIN TRANSFERASE

RELATED APPLICATIONS

The present patent application is a continuation-in-part application of copending application Ser. No. 08/236,903, filed. Apr. 29, 1994, which is a divisional application of application Ser. No. 07/968,106, filed Oct. 29, 1992, which issued as U.S. Pat. No. 5,326,773 on Jul. 5, 1994.

BACKGROUND OF THE INVENTION

The Ras gene is found activated in many human cancers, including colorectal carcinoma, exocrine pancreatic carcinoma, and myeloid leukemias. Biological and biochemical studies of Ras action indicate that Ras functions like a G-regulatory protein, since Ras must be localized in the plasma membrane and must bind with GTP in order to transform cells (Gibbs, J. et al., *Microbiol. Rev.* 53:171–286 (1989). Forms of Ras in cancer cells have mutations that distinguish the protein from Ras in normal cells.

At least 3 post-translational modifications are involved with Ras membrane localization, and all 3 modifications occur at the C-terminus of Ras. The Ras C-terminus contains a sequence motif termed a "CAAX" or "Cys-$Aaa^1$-$Aaa^2$-Xaa" box (Aaa is an aliphatic amino acid, the Xaa is any amino acid) (Willumsen et al., Nature 310:583–586 (1984)). Other proteins having this motif include the Ras-related GTP-binding proteins such as Rho, fungal mating factors, the nuclear lamins, and the gamma subunit of transducin.

Farnesylation of Ras by the isoprenoid farnesyl pyrophosphate (FPP) occurs in vivo on Cys to form a thioether linkage (Hancock et al., *Cell* 57:1167 (1989); Casey et al., *Proc. Natl. Acad. Sci. U.S.A.* 86:8323 (1989)). In addition, Ha-Ras and N-Ras are palmitoylated via formation of a thioester on a Cys residue near a C-terminal Cys farnesyl acceptor (Gutierrez et at., *EMBO J.* 8:1093–1098 (1989); Hancock et al., *Cell* 57:1167–1177 (1989)). Ki-Ras lacks the palmitate acceptor Cys. The last 3 amino acids at the Ras C-terminal end are removed proteolytically, and methyl esterification occurs at the new C-terminus (Hancock et al., *ibid*). Fungal mating factor and mammalian nuclear lamins undergo identical modification steps (Anderegg et al., *J. Biol. Chem.* 263:18236 (1988); Farnsworth et al., *J. Biol. Chem.* 264:20422 (1989)).

Inhibition of Ras farnesylation in vivo has been demonstrated with lovastatin (Merck & Co., Rahway, N.J.) and compactin (Hancock et al., *ibid*; Casey et al., *ibid*; Schafer et at., *Science* 245:379 (1989)). These drugs inhibit HMG-CoA reductase, the rate limiting enzyme for the production of polyisoprenoids and the farnesyl pyrophosphate precursor. It has been shown that a farnesyl-protein transferase using farnesyl pyrophosphate as a precursor is responsible for Ras farnesylation. (Reiss et al., *Cell*, 62:81–88 (1990); Schaber et al., *J. Biol. Chem.*, 265:14701–14704 (1990); Schafer et al., *Science*, 249:1133–1139 (1990); Manne et at., *Proc. Natl. Acad. Sci U.S.A.*, 87:7541–7545 (1990)).

Inhibition of farnesyl-protein transferase and, thereby, of farnesylation of the Ras protein, blocks the ability of Ras to transform normal cells to cancer cells. The compounds of the invention inhibit Ras farnesylation and, thereby, generate soluble Ras which, as indicated infra, can act as a dominant negative inhibitor of Ras function. While soluble Ras in cancer cells can become a dominant negative inhibitor, soluble Ras in normal cells would not be an inhibitor.

A cytosol-localized (no Cys-$Aaa^1$-$Aaa^2$-Xaa box membrane domain present) and activated (impaired GTPase activity, staying bound to GTP) form of Ras acts as a dominant negative Ras inhibitor of membrane-bound Ras function (Gibbs et al., *Proc. Natl. Acad. Sci. U.S.A.* 86:6630–6634(1989)). Cytosollocalized forms of Ras with normal GTPase activity do not act as inhibitors. Gibbs et al., *ibid*, showed this effect in Xenopus oocytes and in mammalian cells.

Administration of compounds of the invention to block Ras farnesylation not only decreases the amount of Ras in the membrane but also generates a cytosolic pool of Ras. In tumor cells having activated Ras, the cytosolic pool acts as another antagonist of membrane-bound Ras function. In normal cells having normal Ras, the cytosolic pool of Ras does not act as an antagonist. In the absence of complete inhibition of farnesylation, other farnesylated proteins are able to continue with their functions.

Farnesyl-protein transferase activity may be reduced or completely inhibited by adjusting the compound dose. Reduction of farnesyl-protein transferase enzyme activity by adjusting the compound dose would be useful for avoiding possible undesirable side effects resulting from interference with other metabolic processes which utilize the enzyme.

These compounds and their analogs are inhibitors of farnesyl-protein transferase. Farnesyl-protein transferase utilizes farnesyl pyrophosphate to covalently modify the Cys thiol group of the Ras CAAX box with a farnesyl group. Inhibition of farnesyl pyrophosphate biosynthesis by inhibiting HMG-CoA reductase blocks Ras membrane localization in vivo and inhibits Ras function. Inhibition of farnesyl-protein transferase is more specific and is attended by fewer side effects than is the case for a general inhibitor of isoprene biosynthesis.

Previously, it has been demonstrated that tetrapeptides containing cysteine as an amino terminal residue with the CAAX sequence inhibit Ras farnesylation (Schaber et al., *ibid*; Reiss et. at., *ibid*; Reiss et al., *PNAS*, 88:732–736 (1991)). Such inhibitors may inhibit while serving as alternate substrates for the Ras farnesyl-transferase enzyme, or may be purely competitive inhibitors (U.S. Pat. No. 5,141, 851, University of Texas).

The compounds of the present invention are peptide analogs containing two reduced peptide bonds and of the general structure C-[ψ$CH_2$NR]$Xaa^1$-[ψ$CH_2$NR]$Xaa^2$-$Xaa^3$ where C is Cysteine and $Xaa^{1-3}$ is any amino acid and the nitrogen between $Xaa^1$ and $Xaa^2$ and optionally the nitrogen between C and $Xaa^1$ are substituted with a non-hydrogen substituent. The compounds of this invention are stable inhibitors of Ras farnesyl-transferase. The presence of the reduced amide linkages confers metabolic stability to these inhibitors such that they are capable of inhibiting ras farnesylation in vivo. Reduction of the first and second peptide bonds may also lead to an unexpected enhancement of intrinsic enzyme-inhibitory activity. Substitution of the reactive nitrogen between $Xaa^1$ and $Xaa^2$ confers chemical stability to these analogs, thus enhancing their activity in vivo (cell culture). Of particular utility is the observation that the lactone or ester forms of these inhibitors are prodrugs that efficiently deliver the active hydroxy acids or acids, respectively, to the intracellular compartment that is the site of Ras farnesylation.

It is, therefore, an object of this invention to develop tetrapeptide-based compounds with two reduced amide linkages, wherein the nitrogen between $Xaa^1$ and $Xaa^2$ is substituted, and which will inhibit farnesyl-protein transferase and the farnesylation of the oncogene protein Ras. It is a further object of this invention to develop chemotherapeutic compositions containing the compounds of this invention, and methods for producing the compounds of this invention.

SUMMARY OF THE INVENTION

The present invention includes tetrapeptide analogs which possess two reduced amide linkages and which inhibit farnesyl-protein transferase and the farnesylation of the oncogene protein Ras, chemotherapeutic compositions containing the compounds of this invention, and methods for producing the compounds of this invention.

The compounds of this invention are illustrated by the formulae:

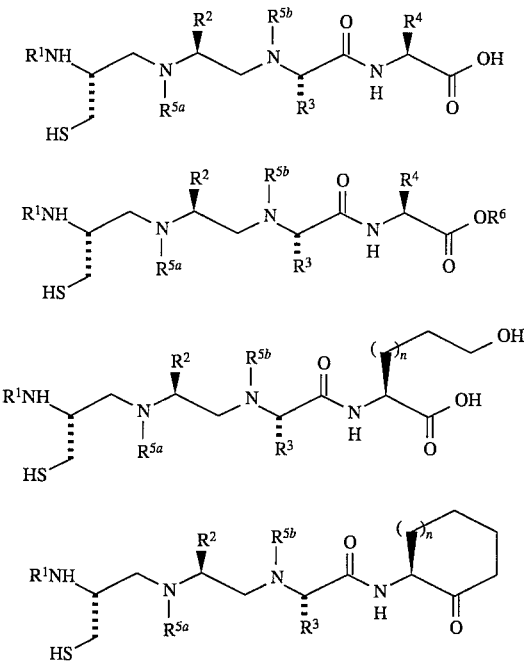

DETAILED DESCRIPTION OF THE INVENTION

The compounds of this invention are useful in the inhibition of farnesyl-protein transferase and the farnesylation of the oncogene protein Ras. In a first embodiment of this invention the inhibitors of farnesyl-protein transferase are illustrated by the formula I:

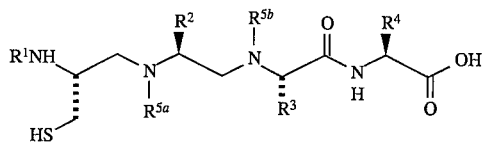

wherein:

$R^1$ and $R^{5a}$ are independently selected from:
  hydrogen, a $C_1$–$C_6$ alkyl group, a $C_1$–$C_6$ acyl group, an aroyl group, a $C_1$–$C_6$ alkylsulfonyl group, $C_1$–$C_6$ aralkylsulfonyl group or arylsulfonyl group wherein the alkyl group and acyl group is optionally substituted with substituted or unsubstituted aryl or heterocycle;

$R^2$, $R^3$ and $R^4$ are independently selected from:
  a) a side chain of naturally occurring amino acids,
  b) an oxidized form of a side chain of naturally occurring amino acids selected from methionine sulfoxide and methionine sulfone,
  c) substituted or unsubstituted $C_1$–$C_8$ alkyl, $C_3$–$C_8$ cycloalkyl, $C_2$–$C_8$ alkenyl, aryl or heterocycle groups, wherein the aliphatic substituent is optionally substituted with an aryl, heterocycle or $C_3$–$C_8$ cycloalkyl;

$R^{5b}$ is a $C_1$–$C_6$ alkyl group, a $C_1$–$C_6$ acyl group, an aroyl group, a $C_1$–$C_6$ alkylsulfonyl group, $C_1$–$C_6$ aralkylsulfonyl group or arylsulfonyl group wherein the alkyl group and acyl group is optionally substituted with substituted or unsubstituted aryl or heterocycle;

and the pharmaceutically acceptable salts thereof.

In a second embodiment of this invention the prodrugs of compounds of formula I are illustrated by the formula II:

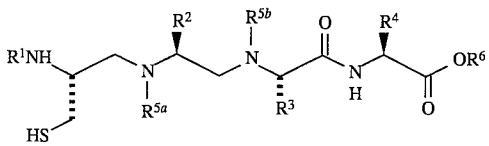

wherein:

$R^1$ and $R^{5a}$ are independently selected from:
  hydrogen, a $C_1$–$C_6$ alkyl group, a $C_1$–$C_6$ acyl group, an aroyl group, a $C_1$–$C_6$ alkylsulfonyl group, $C_1$–$C_6$ aralkylsulfonyl group or arylsulfonyl group wherein the alkyl group and acyl group is optionally substituted with substituted or unsubstituted aryl or heterocycle;

$R^2$, $R^3$ and $R^4$ are independently selected from:
  a) a side chain of naturally occurring amino acids,
  b) an oxidized form of a side chain of naturally occurring amino acids selected from methionine sulfoxide and methionine sulfone,
  c) substituted or unsubstituted $C_1$–$C_8$ alkyl, $C_3$–$C_8$ cycloalkyl, $C_2$–$C_8$ alkenyl, aryl or heterocycle groups, wherein the aliphatic substituent is optionally substituted with an aryl, heterocycle or $C_3$–$C_8$ cycloalkyl;

$R^{5b}$ is a $C_1$–$C_6$ alkyl group, a $C_1$–$C_6$ acyl group, an aroyl group, a $C_1$–$C_6$ alkylsulfonyl group, $C_1$–$C_6$ aralkylsulfonyl group or arylsulfonyl group wherein the alkyl group and acyl group is optionally substituted with substituted or unsubstituted aryl or heterocycle;

$R^6$ is a substituted or unsubstituted aliphatic, aryl or heterocyclic group, wherein the aliphatic substituent is optionally substituted with an aryl or heterocyclic ring;

and the pharmaceutically acceptable salts and disulfides thereof.

In a third embodiment of this invention, the inhibitors of farnesyl-protein transferase are illustrated by the formula III:

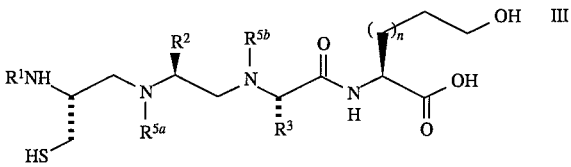

wherein:

$R^1$ and $R^{5a}$ are independently selected from:
  hydrogen, a $C_1$–$C_6$ alkyl group, a $C_1$–$C_6$ acyl group, an aroyl group, a $C_1$–$C_6$ alkylsulfonyl group, $C_1$–$C_6$ aralkylsulfonyl group or arylsulfonyl group wherein the alkyl group and acyl group is optionally substituted with substituted or unsubstituted aryl or heterocycle;

$R^2$ and $R^3$ are independently selected from:
a) a side chain of naturally occurring amino acids,
b) an oxidized form of a side chain of naturally occurring amino acids selected from methionine sulfoxide and methionine sulfone,
c) substituted or unsubstituted $C_1$–$C_8$ alkyl, $C_3$–$C_8$ cycloalkyl, $C_2$–$C_8$ alkenyl, aryl or heterocycle groups, wherein the aliphatic substituent is optionally substituted with an aryl, heterocycle or $C_3$–$C_8$ cycloalkyl;

$R^{5b}$ is a $C_1$–$C_6$ alkyl group, a $C_1$–$C_6$ acyl group, an aroyl group, a $C_1$–$C_6$ alkylsulfonyl group, $C_1$–$C_6$ aralkylsulfonyl group or arylsulfonyl group wherein the alkyl group and acyl group is optionally substituted with substituted or unsubstituted aryl or heterocycle;

n is 0, 1 or 2;
and the pharmaceutically acceptable salts thereof.

In a fourth embodiment of this invention the prodrugs of compounds of formula III are illustrated by the formula IV:

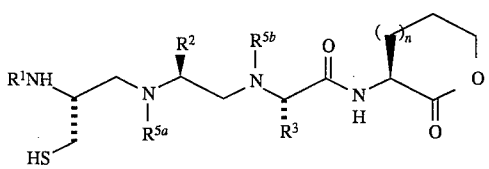

wherein:
$R^1$ and $R^{5a}$ are independently selected from:
hydrogen, a $C_1$–$C_6$ alkyl group, a $C_1$–$C_6$ acyl group, an aroyl group, a $C_1$–$C_6$ alkylsulfonyl group, $C_1$–$C_6$ aralkylsulfonyl group or arylsulfonyl group wherein the alkyl group and acyl group is optionally substituted with substituted or unsubstituted aryl or heterocycle;

$R^2$ and $R^3$ are independently selected from:
a) a side chain of naturally occurring amino acids,
b) an oxidized form of a side chain of naturally occurring amino acids selected from methionine sulfoxide and methionine sulfone,
c) substituted or unsubstituted $C_1$–$C_8$ alkyl, $C_3$–$C_8$ cycloalkyl, $C_2$–$C_8$ alkenyl, aryl or heterocycle groups, wherein the aliphatic substituent is optionally substituted with an aryl, heterocycle or $C_3$–$C_8$ cycloalkyl;

$R^{5b}$ is a $C_1$–$C_6$ alkyl group, a $C_1$–$C_6$ acyl group, an aroyl group, a $C_1$–$C_6$ alkylsulfonyl group, $C_1$–$C_6$ aralkylsulfonyl group or arylsulfonyl group wherein the alkyl group and acyl group is optionally substituted with substituted or unsubstituted aryl or heterocycle;

n is 0, 1 or 2;
and the pharmaceutically acceptable salts and disulfides thereof.

The preferred compounds of this invention are as follows:
N-[2(S)-(2(R)-amino-3-mercaptopropylamino)-3(S)-methylpentyl]-N-methyl-isoleucyl-homoserine,
N-[2(S)-(2(R)-amino-3-mercaptopropylamino)-3(S)-methylpentyl]-N-methyl-isoleucyl-homoserine lactone,
N-[2(S)-(2(R)-amino-3-mercaptopropylamino)-3(S)-methylpentyl]-N-methyl-phenylalanyl-homoserine,
N-[2(S)-(2(R)-amino-3-mercaptopropylamino)-3(S)-methylpentyl]-N-methyl-phenylalanyl-homoserine lactone,
N-[2(S)-(2(R)-amino-3-mercaptopropylamino)-3-methylbutyl]-N-methyl-phenylalanyl-homoserine,
N-[2(S)-(2(R)-amino-3-mercaptopropylamino)-3-methylbutyl]-N-methyl-phenylalanyl-homoserine lactone,
3(S)-{N-[2(S)-(2(R)-amino-3-mercaptopropylamino)-3(S)-methyl-pentyl]-N-methyl-isoleucylamino}- 3-methyltetra-hydropyran-2-one,
2(S)-{N-[2(S)-(2(R)-amino-3-mercaptopropylamino)-3(S)-methyl-pentyl]-N-methyl-isoleucylamino}- 2-methyl-5-hydroxypentanoic acid,
2(S)-{N-[2(S)-(2(R)-amino-3-mercaptopropylamino)-3(S)-methylpentyl]-N-methyl-isoleucylamino}- 5-methyl-5-hydroxyhexanoic acid,
N-[2(S)-(2(R)-amino-3-mercaptopropylamino)-3(S)-methylpentyl]-N-methyl-norvalyl-homoserine,
N-[2(S)-(2(R)-amino-3-mercaptopropylamino)-3(S)-methylpentyl]-N-methyl-norvalyl-homoserine lactone,
N-[2(S)-(2(R)-amino-3-mercaptopropylamino)-3(S)-methylpentyl]-N-methyl-isoleucyl-methionine,
N-[2(S)-(2(R)-amino-3-mercaptopropylamino)-3(S)-methylpentyl]-N-methyl-isoleucyl-methionine methyl ester,
N-[2(S)-(2(R)-amino-3-mercaptopropylamino)-3(S)-methylpentyl]-N-methyl-phenylalanyl-methionine,
N-[2(S)-(2(R)-amino-3-mercaptopropylamino)-3(S)-methylpentyl]-N-methyl-phenylalanyl-methionine methyl ester,
3(S)-{N-[2(S)-(2(R)-amino-3-mercaptopropylamino)-3(S)-methyl-pentyl]-N-methyl-isoleucylamino}- 6,6-dimethyl-tetrahydropyran-2-one,
N-[2(S)-(2(R)-amino-3-mercaptopropylamino)-3(S)-methylpentyl]-N-methyl-norvalyl-methionine,
N-[2(S)-(2(R)-amino-3-mercaptopropylamino)-3(S)-methylpentyl]-N-methyl-norvalyl-methionine methyl ester,
N-[2(S)-(2(R)-amino-3-mercaptopropylamino)-3(S)-methylpentyl]-N-methyl-D-norvalyl-homoserine,
N-[2(S)-(2(R)-amino-3-mercaptopropylamino)-3(S)-methylpentyl]-N-methyl-D-norvalyl-homoserine lactone,
N-[2(S)-(2(R)-amino-3-mercaptopropylamino)-3(S)-methylpentyl]-N-(1-naphthylmethyl)-glycyl methionine,
N-[2(S)-(2(R)-amino-3-mercaptopropylamino)-3(S)-methylpentyl]-N-(1-naphthylmethyl)-glycyl methionine methyl ester,
N-[2(S)-(2(R)-amino-3-mercaptopropylamino)-3(S)-methylpentyl]-N-(1-naphthylmethyl)-glycyl methionine sulfone,
N-[2(S)-(2(R)-amino-3-mercaptopropylamino)-3(S)-methylpentyl]-N-(1-naphthylmethyl)-glycyl methionine sulfone methyl ester,
N-[2(S)-(2(R)-amino-3-mercaptopropylamino)-3(S)-methylpentyl]-N-(1-naphthylmethyl)-glycyl homoserine,
N-[2(S)-(2(R)-amino-3-mercaptopropylamino)-3(S)-methylpentyl]-N-(1-naphthylmethyl)-glycyl homoserine lactone,
N-[2(S)-(2(R)-amino-3-mercaptopropylamino)-3(S)-methylpentyl]-N-benzyl-norvalyl methionine,
N-[2(S)-(2(R)-amino-3-mercaptopropylamino)-3(S)-methylpentyl]-N-benzyl-norvalyl methionine methyl ester,
N-[2(S)-(2(R)-amino-3-mercaptopropylamino)-3(S)-methylpentyl]-N-benzyl-alanyl methionine,
N-[2(S)-(2(R)-amino-3-mercaptopropylamino)-3(S)-methylpentyl]-N-benzyl-alanyl methionine methyl ester,
N-[2(S)-(2(R)-amino-3-mercaptopropylamino)-3(S)-methylpentyl]-N-benzyl-glycyl methionine,
N-[2(S)-(2(R)-amino-3-mercaptopropylamino)-3(S)-methylpentyl]-N-benzyl-glycyl methionine methyl ester,
N-[2(S)-(2(R)-amino-3-mercaptopropylamino)-3(S)-methylpentyl]-N-benzyl-glycyl methionine sulfone,
N-[2(S)-(2(R)-amino-3-mercaptopropylamino)-3(S)-methylpentyl]-N-benzyl-glycyl methionine sulfone methyl ester,
N-[2(S)-(2(R)-amino-3-mercaptopropylamino)-3(S)-methylpentyl]-N-n-butyl-glycyl methionine,
N-[2(S)-(2(R)-amino-3-mercaptopropylamino)-3(S)-methylpentyl]-N-phenethyl-glycyl methionine, N-[2(S)-(2(R)-amino-3-mercaptopropylamino)-3(S)-methylpentyl]-N-phenethyl-glycyl methionine methyl ester,
N-[2(S)-(2(R)-amino-3-mercaptopropylamino)-3(S)-methylpentyl]-N-benzyl-phenylalanyl methionine,
N-[2(S)-(2(R)-amino-3-mercaptopropylamino)-3(S)-methylpentyl]-N-(1-naphthylmethyl)-norvalyl methionine,
N-[2(S)-(2(R)-amino-3-mercaptopropylamino)-3(S)-methylpentyl]-N-(1-naphthylmethyl)-norvalyl methionine methyl ester,
N-[2(S)-(2(R)-amino-3-mercaptopropylamino)-3(S)-methylpentyl]-N-benzyl-D-alanyl methionine,
N-[2(S)-(2(R)-amino-3-mercaptopropylamino)-3(S)-methylpentyl]-N-benzyl-D-alanyl methionine methyl ester,
N-[2(R)-(2(R)-amino-3-mercaptopropylamino)-3(S)-methylpentyl]-N-benzyl-D-alanyl methionine,
N-[2(R)-(2(R)-amino-3-mercaptopropylamino)-3(S)-methylpentyl]-N-benzyl-D-alanyl methionine methyl ester,
N-[2(R)-(2(R)-amino-3-mercaptopropylamino)-3(S)-methylpentyl]-N-benzyl-alanyl methionine,
N-[2(R)-(2(R)-amino-3-mercaptopropylamino)-3(S)-methylpentyl]-N-benzyl-alanyl methionine methyl ester,
N-[2(S)-(2(R)-amino-3-mercaptopropylamino)-3(S)-methylpentyl]-N-(3-quinolylmethyl)-glycyl methionine,
N-[2(S)-(2(R)-amino-3-mercaptopropylamino)-3(S)-methylpentyl]-N-(3-quinolylmethyl)-glycyl methionine methyl ester,
N-[2(S)-(2(R)-amino-3-mercaptopropylamino)-3(S)-methylpentyl]-N-benzoyl-norvalyl methionine,
N-[2(S)-(2(R)-amino-3-mercaptopropylamino)-3(S)-methylpentyl]-N-benzoyl-norvalyl methionine methyl ester,
N-[2(S)-(2(R)-amino-3-mercaptopropyl(methylamino))-3(S)-methylpentyl]-N-(1-naphthylmethyl)-glycyl methionine,
N-[2(S)-(2(R)-amino-3-mercaptopropyl(methylamino))-3(S)-methylpentyl]-N-(1-naphthylmethyl)-glycyl methionine methyl ester,
N-[2(S)-(2(R)-amino-3-mercaptopropylamino)-3(S)-methylpentyl]-N-[1-(5-dimethylamino)naphthylmethylsulfonyl]-glycyl methionine, or
N-[2(S)-(2(R)-amino-3-mercaptopropylamino)-3(S)-methylpentyl]-N-[1-(5-dimethylamino)naphthylmethylsulfonyl]-glycyl methionine methyl ester,
and the pharmaceutically acceptable salts thereof.

The most preferred compounds of this invention include the following inhibitor and corresponding ester/lactone prodrug pairs:

N-[2(S)-(2(R)-amino-3-mercaptopropylamino)-3(S)-methylpentyl]-N-methyl-isoleucyl-homoserine

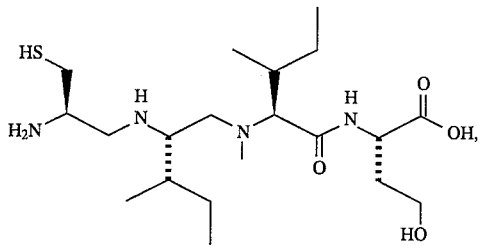

N-[2(S)-(2(R)-amino-3-mercaptopropylamino)-3(S)-methylpentyl]-N-methyl-isoleucyl-homoserine lactone

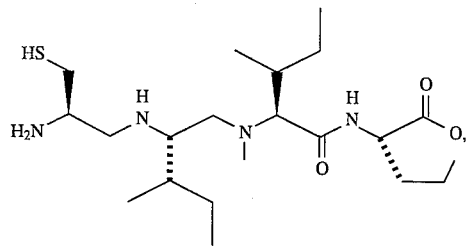

N-[2(S)-(2(R)-amino-3-mercaptopropylamino)-3(S)-methylpentyl]-N-methyl-isoleucyl-methionine

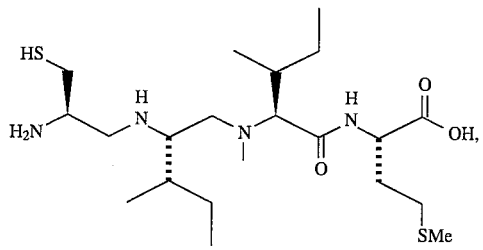

N-[2(S)-(2(R)-amino-3-mercaptopropylamino)-3(S)-methylpentyl]-N-methyl-isoleucyl-methionine methyl ester

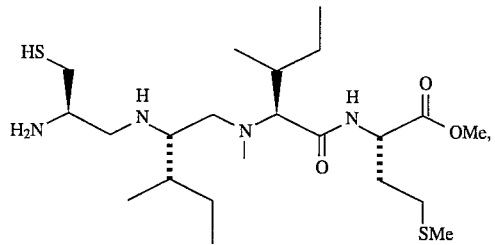

N-[2(S)-(2(R)-amino-3-mercaptopropylamino)-3(S)-methylpentyl]-N-(1-naphthylmethyl)-glycyl-methionine

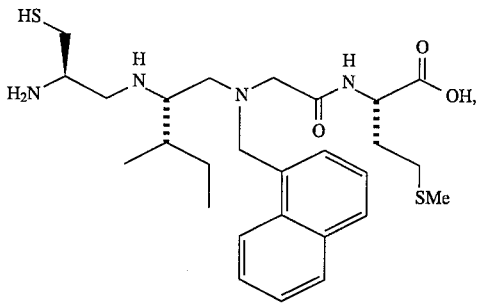

N-[2(S)-(2(R)-amino-3-mercaptopropylamino)-3(S)-methylpentyl]-N-(1-naphthylmethyl)-glycyl-methionine methyl ester

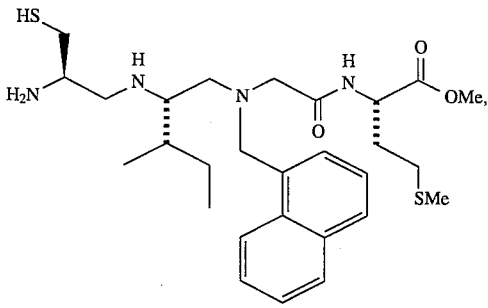

N-[2(S)-(2(R)-amino-3-mercaptopropylamino)-3(S)-methylpentyl]-N-(1-naphthylmethyl)-glycyl-methionine sulfone

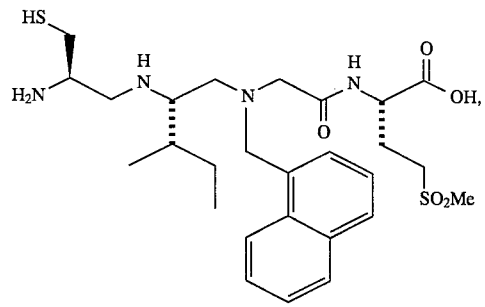

N-[2(S)-(2(R)-amino-3-mercaptopropylamino)-3(S)-methylpentyl]-N-(1-naphthylmethyl)-glycyl-methionine sulfone methyl ester

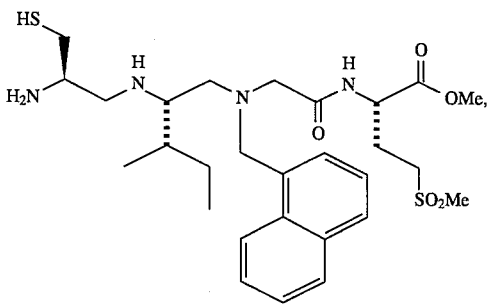

N-[2(S)-(2(R)-amino-3-mercaptopropylamino)-3(S)-methylpentyl]-N-benzyl-glycyl-methionine

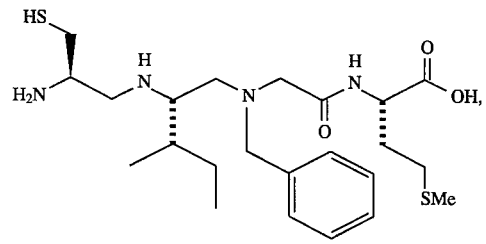

N-[2(S)-(2(R)-amino-3-mercaptopropylamino)-3(S)-methylpentyl]-N-benzyl-glycyl-methionine methyl ester

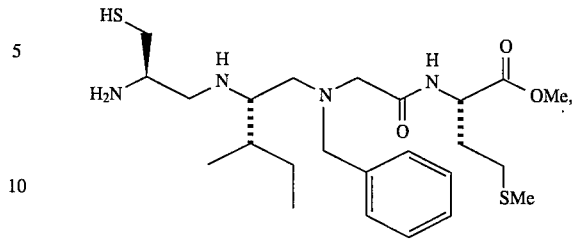

and the pharmaceutically acceptable salts thereof.

In the present invention, the amino acids which are disclosed are identified both by conventional 3 letter and single letter abbreviations as indicated below:

| | | |
|---|---|---|
| Alanine | Ala | A |
| Arginine | Arg | R |
| Asparagine | Asn | N |
| Aspartic acid | Asp | D |
| Asparagine or Aspartic acid | Asx | B |
| Cysteine | Cys | C |
| Glutamine | Gln | Q |
| Glutamic acid | Glu | E |
| Glutamine or Glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

As used herein, "alkyl" is intended to include both branched and straight-chain saturated aliphatic hydrocarbon groups having the specified number of carbon atoms.

As used herein, "cycloalkyl" is intended to include non-aromatic cyclic hydrocarbon groups having the specified number of carbon atoms. Examples of cycloalkyl groups include cyclopropyl, cyclobutyl, cyclopentyl, cyclohexyl and the like.

"Alkenyl" groups include those groups having the specified number of carbon atoms and having one or several double bonds. Examples of alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl, isoprenyl, farnesyl, geranyl, geranylgeranyl and the like.

As used herein, "aliphatic" is intended to include both branched and straight-chain saturated and unsaturated aliphatic hydrocarbon groups having the specified number of carbon atoms and includes alkyl and alkenyl.

As used herein, "aralkyl" is intended to include both branched and straight-chain saturated aliphatic hydrocarbon groups having the specified number of carbon atoms and having an aryl group as a substituent.

As used herein, "aracyl" is intended to include both branched and straight-chain saturated aliphatic hydrocarbon groups having the specified number of carbon atoms, wherein the carbon atom which is at the point of attachment is part of a carbonyl group and having an aryl group as a substituent.

As used herein, "aryl" is intended to include any stable monocyclic, bicyclic or tricyclic carbon ring(s) of up to 7 members in each ring, wherein at least one ring is aromatic. Examples of aryl groups include phenyl, naphthyl, anthracenyl, biphenyl, tetrahydronaphthyl, indanyl, phenanthrenyl and the like.

The term heterocycle or heterocyclic, as used herein, represents a stable 5- to 7-membered monocyclic or stable 8- to 11-membered bicyclic or stable 11–15 membered tricyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothio-pyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopiperazinyl, 2-oxopiperidinyl, 2-oxopyrrolidinyl, piperidyl, piperazinyl, pyridyl, pyridyl N-oxide, pyridonyl, pyrazinyl, pyrazolidinyl, pyrazolyl, pyrimidinyl, pyrrolidinyl, pyrrolyl, quinazolinyl, quinolinyl, quinolinyl N-oxide, quinoxalinyl, tetrahydrofuryl, tetrahydroisoquinolinyl, tetrahydro-quinolinyl, thiamorpholinyl, thiamorpholinyl sulfoxide, thiazolyl, thiazolinyl, thienofuryl, thienothienyl, and thienyl.

As used herein, the terms "substituted aryl", "substituted heterocycle" and "substituted cycloalkyl" are intended to include the cyclic group which is substituted with 1 or 2 substitutents selected from the group which includes but is not limited to F, Cl, Br, CF$_3$, NH$_2$, N(C$_1$–C$_6$ alkyl)$_2$, NO$_2$, CN, (C$_1$–C$_6$ alkyl)O—, —OH, (C$_1$–C$_6$ alkyl)S(O)$_m$—, (C$_1$–C$_6$ alkyl)C(O)NH—, H$_2$N—C(NH)—, (C$_1$–C$_6$ alkyl)C(O)—, (C$_1$–C$_6$ alkyl)OC(O)—, N$_3$, (C$_1$–C$_6$ alkyl)O-C(O)NH— and C$_1$–C$_{20}$ alkyl.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic moiety by conventional chemical methods. Generally, the salts are prepared by reacting the free base with stoichiometric amounts or with an excess of the desired salt-forming inorganic or organic acid in a suitable solvent or various combinations of solvents.

The compounds of the invention can be synthesized from their constituent amino acids by conventional peptide synthesis techniques, and the additional methods described below. Standard methods of peptide synthesis are disclosed, for example, in the s following works: Schroeder et al., "The Peptides", Vol. I, Academic Press 1965, or Bodanszky et at., "Peptide Synthesis", Interscience Publishers, 1966, or McOmie (ed.) "Protective Groups in Organic Chemistry", Plenum Press, 1973, or Barany et al., "The Peptides: Analysis, Synthesis, Biology" 2, Chapter 1, Academic Press, 1980, or Stewart et al., "Solid Phase Peptide Synthesis", Second Edition, Pierce Chemical Company, 1984. The teachings of these works are hereby incorporated by reference.

Compounds of this invention are prepared by employing reactions A through C as shown in the Reaction Scheme, in addition to other standard manipulations such as ester hydrolysis, cleavage of protecting groups, etc., as may be known in the literature or exemplified in the experimental procedures. The key bond-forming reactions are:

Reaction A. Amide bond formation and protecting group cleavage using standard solution or solid phase methodologies.

Reaction B. Preparation of a reduced peptide subunit by reductive alkylation of an amine by an aldehyde using sodium cyanoborohydride or other reducing agents.

Reaction C. Alkylation of a reduced peptide subunit with an alkyl or aralkyl halide or, alternatively, reductive alkylation of a reduced peptide subunit with an aldehyde using sodium cyanoborohydride or other reducing agents.

These reactions may be employed in a linear sequence to provide the compounds of the invention or they may be used to synthesize fragments which are subsequently joined by the alkylation reactions described in the Reaction Scheme.

REACTION SCHEME A

Reaction A. Coupling of residues to form an amide bond

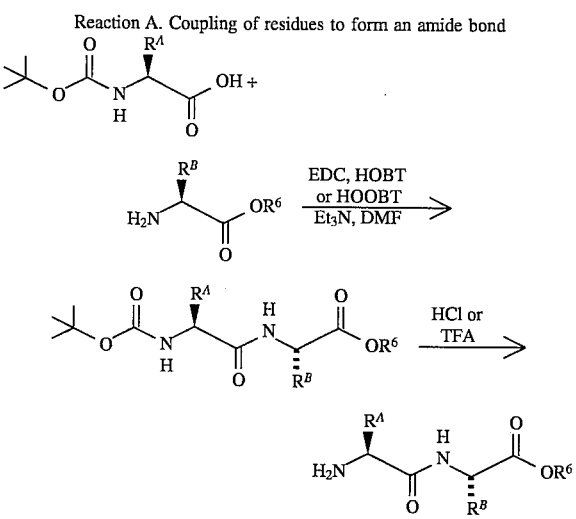

REACTION SCHEME C

Reaction C.
Alkylation/reductive alkylation of reduced peptide subunits

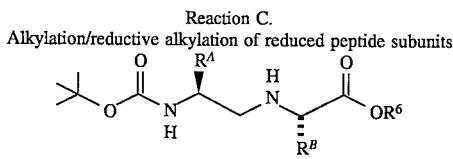

-continued
REACTION SCHEME C

Reaction C.
Alkylation/reductive alkylation of reduced peptide subunits

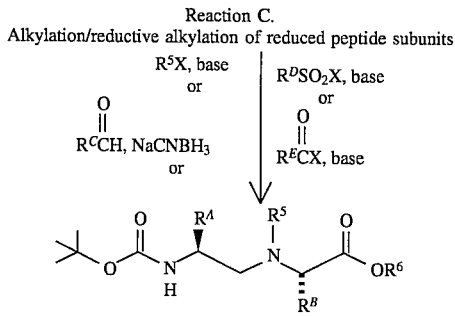

where $R^A$ and $R^B$ are $R^2$, $R^3$ or $R^4$ as previously defined; X is a leaving group, e.g., $Br^-$, $I^-$ or $MsO^-$; and $R^C$, $R^D$ and $R^E$ are defined such that $R^5$ is generated by the reductive alkylation, acylation and sulfonylation processes. It is understood that substitution on an amine nitrogen can take place sequentially; thus the product from Reaction Scheme C can be deprotected and undergo the reductive alkylation as illustrated in Reaction Scheme B and then again undergo a substitution reaction as shown in Reaction Scheme C.

The compounds of this invention inhibit farnesyl-protein transferase and the farnesylation of the oncogene protein Ras. These compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carders which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 20 mg/kg of body weight per day, preferably of between 0.5 mg/kg of body weight to about 10 mg/kg of body weight per day.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof.

EXAMPLE 1

Preparation of
N-[2(S)-(2(R)-Amino-3-mercaptopropyl-amino)-3(S)-methylpentyl]-N-methyl-isoleucyl-homoserine lactone and N-[2(S)-(2(R)-Amino-3-mercaptopropylamino)-3(S)-methylpentyl]-N-methyl-isoleucyl-homoserine Step A: N-(t-butoxycarbonyl)-isoleucine aldehyde This compound was synthesized by applying the procedure of Goel, Krolls, Stier, and Kesten [Organic Syntheses, 67, 69 (1988)] to N-(t-butoxycarbonyl)-isoleucine. The compound was obtained as a colorless oil, which was used without purification.

Step B:
N-[(2S)-(t-Butoxycarbonylamino)-3(S)-methyl-pentyl)-isoleucine benzyl ester N-(t-Butoxycarbonyl)-isoleucine aldehyde (8.0 g, 0.037 mol) and isoleucine benzyl ester p-toluenesulfonate salt (19.0 g, 0.048 mol) were dissolved in MeOH (50 mL) at ambient temperature under nitrogen and treated with 3A molecular sieves (15 g) and sodium triacetoxyborohydride (20.4 g, 0.096 mol) with stirring. After 2 h the mixture was filtered, concentrated, and the residue was partitioned between EtOAc (100 mL) and satd aq NaHCO$_3$ soln (100 mL). The basic layer was washed with EtOAc (2×50 mL), the organics combined, washed with brine, and dried (Na$_2$SO$_4$). Filtration and concentration to dryness gave 6.4 g (41%) of the title compound as a white solid after chromatography (SiO$_2$, hexane: EtOAc, 9:1).

$^1$H NMR (CD$_3$OD) δ7.30–7.45 (m, 5H), 5.18 (ABq, 2H), 3.40–3.45 (m, 1H), 3.12 (d, 1H, J=6 Hz), 2.70 (dd, 1H, J=4, 12 Hz), 2.37 (dd, 1H, J=4, 12 Hz), 2.63–2.76 (m, 1H), 1.45–1.61 (m, 2H), 1.46 (s, 9H), 1.05–1.26 (m, 2H), 0.82–0.95 (m, 12H).

Step C:
N-[(2S)-(t-Butoxycarbonylamino)-3(S)-methyl-pentyl)-N-methyl-isoleucine benzyl ester N-[(2S)-(t-Butoxycarbonylamino)-3(S)-methylpentyl)-isoleucine benzyl ester (0.8 g, 1.9 mmol) was dissolved in acetone (3 mL), treated with K$_2$CO$_3$ (0.52 g, 3.8 mmol) and iodomethane (1.2 mL, 19 mmol) and stirred for 18 h at ambient temperature. The reaction mixture was treated with 5% aq NH$_4$OH soln (10 mL), stirred for 0.5 h, concentrated, and partitioned between EtOAc (20 mL) and H$_2$O (20 mL). The aq layer was washed with EtOAc (2×20 mL), organics combined, washed sequentially with H$_2$O, 10% citric acid, brine, and dried (Na$_2$SO$_4$). Filtration and concentration to dryness gave 0.814 g (98%) of the title compound as a yellow oil. $^1$H NMR (CDCL$_3$) δ7.32–7.41 (m, 5H), 5.11–5.24 (m, 2H), 3.58–3.72 (m, 1H), 2.8–3.0 (m, 1H), 2.20–2.65 (m, 5H), 1.88–2.0 (m, 1H), 1.68–1.80 (m, 1H), 1.56–1.67 (m, 1H), 1.45 (s, 9H), 1.29–1.42 (m, 2H), 1.12–1.28 (m, 1H), 0.98–1.09 (m, 1H), 0.80–0.95 (m, 12H).

Step D:
N-[(2S)-(t-Butoxycarbonylamino)-3(S)-methyl-pentyl)-N-methyl-isoleucine N-[(2S)-(t-Butoxycarbonylamino)-3(S)-methyl-pentyl)-N-methyl-isoleucine benzyl ester (0.814 g, 1.87 mmol) was dissolved in methanol (25 mL)—EtOAc (25 mL), treated with 10% palladium on carbon (0.1 g) and hydrogenated under a balloon of hydrogen for 4 h. Filtration and concentration to dryness gave 0.614 g (95%) of the title compound as a white solid. $^1$H NMR (CDCl$_3$) δ5.1–5.2 (m, 1H), 3.7–3.8 (m, 1H), 3.27–3.35 (m, 1H), 2.8–2.92 (m, 2H), 2.55 (s, 3H), 1.80–1.93 (m, 1H), 1.55–1.8 (m, 2H), 1.48 (s, 9H), 1.23–1.42 (m, 1H), 1.05–1.2 (m, 1H), 0.82–1.03 (m, 12H).

Step E:
N-[2(S)-(t-butoxycarbonylamino-3(S)-methyl-pentyl]-N-methyl-isoleucyl-homoserine lactone N-[(2S)-(t-Butoxycarbonylamino)-3(S)-methyl-pentyl)-N-methyl-isoleucine (1.05g, 3.05 mmol) was dissolved in DMF (10 mL) with stirring at ambient temperature and treated with EDC (0.64 g, 3.35 mmol), HOBT (0.45 g, 3.35 mmol), and homoserine lactone hydrochloride. The pH was adjusted to 6 with Et$_3$N (0.40 mL, 2.9 mmol) and stirring was continued for 18 h. The reaction mixture was concentrated, then partitioned between EtOAc (50 mL)—H$_2$O (50 mL). The aq layer was washed with EtOAc (3×20 mL), the organics combined, washed with aq satd NaHCO$_3$ soln, brine, and dried (Na$_2$SO$_4$). Filtration and concentration gave 0.78 g (60%) of the title compound after chromatography (SiO$_2$, hexane: EtOAc, 3:1 to 2:1 to EtOAc). $^1$H NMR (CD$_3$OD) δ4.59 (t, 1H, J=10 Hz), 4.47 (td, 1H, J=2, 10 Hz), 4.28–4.39 (m, 2H), 3.56–3.64 (m, 1H), 2.74 (d, 1H, J=10 Hz), 2.5–2.7 (m, 2H), 2.3–2.42 (m, 2H), 2.29 (s, 3H), 1.75–1.92 (m, 2H), 1.4–1.6 (m, 2H), 1.46 (s, 9H), 1.07–1.20 (m, 2H), 0.88–0.95 (m, 12H).

Step F: N-[2(S)-amino-3(S)-methylpentyl]-N-methyl-isoleucyl-homoserine lactone HCl gas was bubbled into a solution of N-[2(S)-(t-butoxycarbonylamino)- 3(S)-methylpentyl]-N-methyl-isoleucyl-homoserine lactone (0.21 g, 0.5 mmol) in EtOAc (50 mL) with stirring at −20° C. over 0.5 h. The soln was purged with argon for 0.5 h, then concentrated to give 0.21 g (100%) of the title compound as a white solid. $^1$H NMR (CD$_3$OD) δ4.46–5.05 (m, 2H), 4.28–4.38 (m, 1H), 3.54–3.70 (m, 2H), 3.2–3.4 (m, 2H), 2.75–2.97 (m, 3H), 2.45–2.59 (m, 2H), 2.1–2.2 (m, 1H), 1.72–1.92 (m, 2H), 1.50–11.63 (m, 1H), 1.18–1.4 (m, 2H), 0.98–1.12 (m, 12H).

Step G: Preparation of N-(t-butoxycarbonyl)-S-triphenylmethyl cysteine aldehyde This compound was synthesized by applying the procedure of Goel, Krolls, Stier, and Kesten [Organic Syntheses, 67, 69(1988)] to N-(t-butoxycarbonyl)-S-trityl cysteine. The compound was obtained as a white solid, which was used without purification. $^1$H NMR (CDCl$_3$) δ9.2 (1H, s), 7.5–7.1 (18H, m), 5.1 (1H, br d), 3.92 (1H, m), 2.85–2.5 (2H, m), 1.4 (9H, s).

Step H: N-[2(S)-(2(R)-(t-butoxycarbonylamino)-3-triphenylmethyl mercaptopropylamino)-3(S)-methylpentyl]-N-methyl-isoleucyl-homoserine lactone N-[2(S)-amino-3(S)-methylpentyl]-N-methyl-isoleucyl-homoserine lactone (0.21 g, 0.6 mmol) was dissolved in methanol (3 mL), treated with KOAc (0.1 g, 1.0 mmol), 3A molecular sieves (0.5 g), and N-(t-butoxycarbonylamino)-S-triphenylmethylcysteine aldehyde (0.25 g, 0.6 mmol) followed by sodium cyanoborohydride (1M in THF) (1 mL) and stirred at ambient temperature for 18 h. The reaction mixture was filtered and partitioned between EtOAc (20 mL) and aq satd NaHCO$_3$ soln. The organic layer was washed with brine and dried (Na$_2$SO$_4$). Filtration and concentration to dryness gave a solid product which was chromatographed (SiO$_2$, CH$_2$Cl$_2$: MeOH, 99:1 to 97:3) to give 0.12 g (33%) of the title compound. $^1$H NMR (CD$_3$OD) δ7.21–7.42 (m, 15H), 4.42–4.56 (m, 2H), 4.25–4.34 (m, 1H), 3.62–3.72 (m, 1H), 2.63–2.80 (m, 3H), 2.30–2.60 (m, 6H), 2.18–2.28 (m, 4H), 1.81–1.93 (m, 1H), 1.54–1.78 (m, 2H), 1.45 (s, 9h), 1.06–1.37 (m, 3H), 0.80–0.98 (m, 12H).

Step I:
N-[2(S)-(2(R)-Amino-3-mercaptopropylamino)-3(S)-methylpentyl]-N-methyl-isoleucyl-homoserine lactone N-[2(S)-(2(R)-(t-butoxycarbonylamino)-3-triphenylmethyl mercaptopropylamino)-3(S)-methylpentyl]-N-methyl-isoleucyl-homoserine lactone (0.12 g, 0.16 mmol) was dissolved in CH$_2$Cl$_2$ (5 mL), treated with CF$_3$CO$_2$H (TFA) (2.5 mL) and triethylsilane (0.10 mL, 0.64 mmol), and stirred at ambient temperature for 0.5 h. The soln was concentrated to dryness and triturated with 0.1% TFA in H$_2$O. The solid triphenylmethane was removed by filtration and the filtrate was lyophilized to give 0.07 g (59%) of the title compound. $^1$H NMR (CD$_3$OD) δ4.45–4.55 (m, 2H), 4.28–4.35 (m, 1H), 3.52–3.61 (m, 1H), 3.49 (d, 1H, J=6 Hz), 3.18–3.25 (m, 1H), 3.02–3.16 (m, 4H), 2.92 (t, 1H, J=6 Hz), 2.85 (t, 1H, J=6 Hz), 2.78 (s, 3H), 2.42–2.56 (m, 2H), 2.05–2.15 (m, 1H), 1.83–1.94 (m, 1H), 1.58–1.61 (m, 1H), 1.40–1.52 (m, 1H), 1.22–1.4 (m, 2H), 0.93–1.06 (m, 12H). Anal. Calcd for C$_{20}$H$_{40}$N$_4$O$_3$S.3CF$_3$CO$_2$H.0.6 H$_2$O: C, 40.72; H, 5.77; N, 7.31. Found: C, 40.72; H, 5.99; N, 7.69.

Step J:
N-[2(S)-(2(R)-Amino-3-mercaptopropylamino)-3(S)-methylpentyl]-N-methyl-isoleucyl-homoserine N-[2(S)-(2(R)-Amino-3-mercaptopropylamino)-3(S)-methylpentyl]-N-methyl-isoleucyl-homoserine lactone (0.0025 g, 0.00326 mmol) was dissolved in MeOH (0.0506 mL) and 1N NaOH (0.0134 mL) was added followed by MeOH (0.262 mL). Conversion of the lactone to the hydroxy-acid was confirmed by HPLC analysis and/or $^1$H NMR spectroscopy.

EXAMPLE 2

Preparation of
N-[2(S)-(2(R)-Amino-3-mercaptopropyl-amino)-3(S)-methylpentyl]-N-methyl-phenylalanyl-homoserine lactone and N-[2(S)-(2(R)-Amino-3-mercapto-propylamino)-3(S)-methylpentyl]-N-methyl-phenylalanyl-homoserine The title compounds were prepared according to the methods of Example 1, substituting phenylalanine methyl ester for the isoleucine benzyl ester used in Step B. Step D was replaced by a hydrolysis of the methyl ester as outlined below.

Step D: N-[(2S)-(t-Butoxycarbonylamino)-3(S)-methyl-pentyl)-N-methyl-phenylalanine N-[(2S)-(t-Butoxycarbonylamino)-3(S)-methyl-pentyl)-N-methyl-phenylalanine methyl ester (1.92 g, 0.0049 mol) was dissolved in MeOH (20 mL), treated with 4 equivalents of 1N NaOH (19.56 mL, 0.0196 mol), and stirred at ambient temperature for 18 h. The reaction mixture was concentrated to remove the methanol, then neutralized with 1N HCl (19.56 mL, 0.0196 mol), and extracted with EtOAc (3×30 mL). The organics were combined, washed with brine and dried (Na$_2$SO$_4$). Filtration and concentration to dryness gave 1.6 g (86%) of the title compound which was used without further purification. Using Steps E-I of Example 1, the title compound was obtained as its trifluoroacetate salt, mp 74°–80° C. $^1$H NMR (CD$_3$OD) δ7.2–7.4 (m, 5H), 4.41–4.48 (m, 1H), 4.24 (q, 1H, J=9 Hz), 4.15 (t, 1H, 11 Hz), 3.97 (dd, 1H, J=6, 11 Hz), 3.53 (t, 1H, J=6 Hz), 2.95–3.4 (m, 8H), 2.82–2.92 (m, 1H), 2.81 (s, 3H), 2.12–2.3 (m, 2H), 1.82–1.95 (m, 1H), 1.35–1.52 (m, 1H), 1.15–1.23 (m, 1H), 0.85–1.03 (m, 6H). Anal. calculated for C$_{23}$H$_{38}$N$_4$O$_3$S.2.85 CF$_3$CO$_2$H: C, 44.44; H, 5.31; N, 7.22; Found: C, 44.36; H, 5.46; N, 7.50.

The lactone was converted to the hydroxy acid by the method of Example 1, Step J.

EXAMPLE 3

Preparation of
N-[2(S)-(2(R)-Amino-3-mercaptopropyl-amino)-3-methylbutyl]-N-methyl-phenylalanyl-homoserine lactone and N-[2(S)-(2(R)-Amino-3-mercaptopropylamino)-3-methylbutyl]-N-methylphenylalanyl-homoserine The title compounds were prepared according to the methods of Example 1 and 2, substituting N-t-butoxycarbonylvaline for the isoleucine derivative used in Step A. The homoserine lactone was obtained as its trifluoroacetate salt, mp 55°–60° C. $^1$H NMR (CD$_3$OD) δ7.21–7.39 (m, 5H), 4.43 (td, 1H, J=4, 10 Hz), 4.22 (q, 1H, J=9 Hz), 4.12 (t, 1H, J=10 Hz), 3.50–3.58 (m, 1H), 3.02–3.35 (m, 8H), 2.82–2.90 (m, 2H), 2.82 (s, 3H), 2.04–2.28 (m, 3H), 1.05 (d, 3H, J=6 Hz), 0.98 (d, 3H, J=6 Hz). Anal. calculated for C$_{22}$H$_{36}$N$_4$O$_3$S.3CF$_3$CO$_2$H.H$_2$O C, 42.21; H, 5.19; N, 7.03; Found: C, 42.17; H, 5.03; N, 7.26.

The hydroxy acid was generated in situ according to Example 1, Step J.

EXAMPLE 4

N-[2(S)-(2(R)-amino-3-mercaptopropylamino)-3(S)-methylpentyl]-N-methyl-norvalyl-homoserine lactone and
N-[2(S)-(2(R)-amino-3-mercaptopropylamino)-3(S)-methylpentyl]-N-methyl-norvalyl-homoserine The title compounds were prepared according to the methods of Examples 1 and 2, substituting norvaline methyl ester for the isoleucine benzyl ester used in Step B. The homoserine lactone was obtained as its trifluoroacetate salt, mp 50°–55° C. $^1$H NMR (CD$_3$OD) δ4.45–4.51 (m, 2H), 4.25–4.38 (m, 1H), 3.75–3.82 (m, 1H), 3.43 (t, 1H, J=6 Hz), 2.82–3.15 (m, 7H), 2.88 (s, 3H), 2.4–2.55 (m, 2H), 1.78–1.97 (m, 3H), 1.32–1.48 (m, 3H), 1.15–1.32 (m, 1H), 1.01 (q, 6H, J=9 Hz), 1.90 (d, 3H, J=7 Hz). Anal. calculated for C$_{19}$H$_{38}$N$_4$O$_3$S. 3CF$_3$CO$_2$H.0.75 H$_2$O: C, 39.60; H, 5.65; N, 7.39; Found: C, 49.58; H, 5.65; N, 7.48.

The hydroxy acid was generated in situ according to Example 1, Step J.

EXAMPLE 5

N-[2(S)-(2(R)-amino-3-mercaptopropylamino)-3(S)-methyl-pentyl]-N-methyl-isoleucyl-methionine methyl ester The title compound was prepared according to the methods of Example 1, Steps A–I, substituting methionine methyl ester for homoserine lactone in Step E. The trifluoroacetate salt was obtained after lyophilization. $^1$H NMR (CD$_3$OD) δ4.65–4.73 (m, 1H), 3.75 (s, 3H), 3.42–3.54 (m, 2H), 2.87–3.22 (m, 7H), 2.73 (s, 3H), 2.49–2.58 (m, 2H), 2.12–2.25 (m, 1H), 2.10 (s, 3H), 1.98–2.1 (m, 2H), 1.8–1.92 (m, 1H), 1.62–1.77 (m, 1H), 1.21–1.48 (m, 3H), 0.9–1.05 (m, 12H). Anal. calculated for C$_{22}$H$_{46}$N$_4$O$_3$S$_2$.2.25 CF$_3$CO$_2$H: C, 43.28; H, 6.61; N, 7.62; Found: C, 43.23; H, 6.54; N, 7.81.

EXAMPLE 6

N-[2(S)-(2(R)-amino-3-mercaptopropylamino)-3(S)-methyl-pentyl]-N-methyl-isoleucyl-methionine

Step A: N-[2(S)-(2(R)-(t-butoxycarbonylamino-3-triphenylmethyl-mercaptopropylamino)-3(S)-methylpentyl]-N-methyl-isoleucyl-methionine N-[2(S)-(2(R)-(t-butoxycarbonylamino-3-triphenylmethyl mercaptopropylamino)-3(S)-methylpentyl]-N-methyl-isoleucyl-methionine methyl ester (0.19 g, 0.232 mmol, prepared as an intermediate in Example 5) was dissolved in MeOH (4 mL), treated with 1N NaOH soln (0.927 mL, 0.927 mmol), and stirred for 3.5 h at ambient temperature. The reaction mixture was concentrated, the residue dissolved in H$_2$O (20 mL), neutralized with 1N HCl (0.927 mL, 0.927 mmol), and extracted with EtOAc (3×20 mL). The organic layers were combined, washed with brine, and dried (Na$_2$SO$_4$). Filtration and concentration to dryness gave 0.18g (96%) of the title compound which was used without further purification.

Step B: N-[2(S)-(2(R)-amino-3-mercaptopropylamino)-3(S)-methylpentyl]-N-methyl-isoleucyl-methionine N-[2(S)-(2(R)-(t-butoxycarbonylamino-3-triphenyl-methylmercaptopropylamino)- 3(S)-methylpentyl]-N-methyl-isoleucyl-methionine (0.18 g, 0.223 mmol) was dissolved in CH$_2$Cl$_2$ (4 mL), treated with CF$_3$CO$_2$H (2 mL) and triethylsilane (0.143 mL, 0.893 mmol) and stirred at ambient temperature for 1.5 h. The reaction mixture was concentrated, partitioned between hexane (20 mL) and 0.1% TFA in H$_2$O (20 mL), the aqueous layer lyophilized to give crude product which was purified by preparative HPLC and re-lyophilized to give 0.075 g (43%) of the title compound as the trifluoroacetate salt. $^1$H NMR (CD$_3$OD) δ4.59–4.68 (m, 1H), 3.47–3.6 (m, 2H), 3.16 (d, 1H, J=6 Hz), 3.06 (s, 3H), 2.85–3.03 (m, 3H), 2.77 (s, 3H), 2.5–2.7 (m, 2H), 2.17–2.29(m, 1H), 2.11 (s, 3H), 1.98–2.1 (m, 2H), 1.8–1.93 (m, 1H), 1.58–1.75 (m, 1H), 1.2–1.5 (m, 3H), 0.85–1.05 (m, 12H). Anal. calculated for C$_{21}$H$_{44}$N$_4$O$_3$S$_2$.2.75 CF$_3$CO$_2$H C, 40.89; H, 6.05; N, 7.20; Found: C, 41.18; H, 6.21; N, 7.25.

EXAMPLE 7

N-[2(S)-(2(R)-amino-3-mercaptopropylamino)-3(S)-methyl-pentyl]-N-methyl-phenylalanyl-methionine methyl ester The title compound was prepared according to the methods of Example 5, substituting phenylalanine methyl ester for isoleucine benzyl ester in Step B, and isolated as its trifluoroacetate salt. $^1$H NMR (CD$_3$OD) δ7.26–7.37 (m, 5H), 4.49–4.55 (m, 1H), 4.16 (t, 1H, J=8 Hz), 3.70 (s, 3H), 3.53 (t, 1H, J=6 Hz), 2.9–3.3 (m, 7H), 2.89 (d, 2H, J=6 Hz), 2.70 (s, 3H), 2.24–2.6 (m, 2H), 2.05 (s, 3H), 1.8–2.17 (m, 3H), 1.33–1.48 (m, 1H), 1.18–1.3 (m, 1H), 0.9–1.0 (m, 6H). MS (M+1) 513.

EXAMPLE 8

N-[2(S)-(2(R)-amino-3-mercaptopropylamino)-3(S)-methylpentyl]-N-methyl-phenylalanyl-methionine The title compound was prepared via an intermediate obtained in Example 7, according to the methods of Example 6 and isolated as its trifluoroacetate salt. $^1$H NMR (CD$_3$OD) δ7.24–7.4 (m, 5H), 4.4–4.5 (m, 1H), 4.12 (t, 1H, J=8 Hz), 3.45–3.52 (m, 1H) 2.8–3.25 (m, 7H), 2.66 (s, 3H), 2.6–2.7 (m, 1H), 2.23–2.5 (m, 2H), 2.05–2.2 (m, 1H), 2.04 (s, 3H), 1.9–2.04 (m, 2H) 1.76–1.9 (m, 1H), 1.12–1.46 (m, 2H), 0.85–1.0 (m, 6H). Anal. calculated for C$_{24}$H$_{42}$N$_4$O$_3$S$_2$.3CF$_3$CO$_2$H.0.5 CH$_3$CN: C, 43.22; H, 5.44; N, 7.32; Found: C, 43.22; H, 5.67; N, 7.68.

EXAMPLE 9

N-[2(S)-(2(R)-amino-3-mercaptopropylamino)-3(S)-methylpentyl]-N-methyl-norvalyl-methionine methyl ester The title compound was prepared according to the methods of Examples 1 and 2, substituting norvaline methyl ester for isoleucine benzyl ester in Step B, methionine methyl ester for homoserine lactone in Step E and substituting the following alternative procedure for Step C.

Step C: N-[(2S)-(t-Butoxycarbonylamino)-3(S)-methyl-pentyl)-N-methyl-norvaline methyl ester N-[(2S)-(t-Butoxycarbonylamino)-3(S)-methyl-pentyl)-norvaline methyl ester (1.15 g, 3.6 mmol) was dissolved in MeOH (15 mL), treated with acetic acid (0.21 mL, 3.6 mmol), formaldehyde (37% in H$_2$O) (0.61 mL, 7.2 mmol) and sodium cyanoborohydride (0.34 g, 5.4 mmol) with stirring under argon at ambient temperature. After 4 h the reaction mixture was concentrated, partitioned between EtOAc (20 mL)—aq satd NH$_4$OH soln (20 mL), and the organic layer dried (Na$_2$SO$_4$) and concentrated to give 1.03 g (83%) of the title compound as a colorless oil. $^1$H NMR (CD$_3$OD) δ3.68 (s, 3H), 3.52–3.6 (m, 1H), 3.27 (t, 1H, J=8Hz), 2.66 (dd, 1H, J=5, 12 Hz), 2.42 (dd, 1H, J=5, 12 Hz), 2.28 (s, 3H), 1.57–1.69 (m, 3H), 1.44 (s, 9H), 1.2–1.5 (m, 3H), 1.0–1.2 (m, 1H), 0.86–1.0 (m 9H).

Following Example 1, Steps D through I, the title compound was isolated as its hydrochloride salt. $^1$H NMR (CD$_3$OD) δ4.66–4.72 (m, 1H), 3.89–3.95 (m, 1H), 3.74 (s, 3H), 3.45–3.6 (m, 1H), 3.1–3.4 (m, 4H), 2.94 (s, 3H), 2.89–3.2 (m, 3H), 2.58–2.73 (m, 2H), 2.12 (s, 3H), 1.88–2.25 (m, 4H), 1.2–1.65 (m, 5H), 0.91–1.1 (m, 9H). Anal. calculated for C$_{21}$H$_{44}$N$_4$O$_3$S$_2$.4.5 HCl: C, 40.11; H, 7.77; N, 8.91; Found: C, 40.03; H, 7.86; N, 8.65.

EXAMPLE 10

N-[2(S)-(2(R)-amino-3-mercaptopropylamino)-3(S)-methylpentyl]-N-methyl-norvalyl-methionine The title compound was prepared from the precursor to Example 9 after hydrolysis and deprotection according to the methods of Example 6 and isolated as its trifluoroacetate salt. $^1$H NMR (CD$_3$OD) δ4.57–4.66 (m, 1H), 3.80 (t, 1H, J=8 Hz), 3.04–3.5 (m, 7H), 2.8–2.97 (m, 4H), 2.90 (s, 3H), 2.47–2.7 (m, 2H), 2.13–2.3 (m, 1H), 2.09 (s, 3H), 1.8–2.0 (m, 2H), 1.34–1.6 (m, 2H), 1.2–1.32 (m, 1H), 0.88–1.1 (m, 9H). Anal. calculated for C$_{20}$H$_{42}$N$_4$O$_3$S$_2$.3CF$_3$CO$_2$H.H$_2$O:

C, 38.51; H, 5.84; N, 6.91; Found: C, 38.51; H, 5.71; N, 7.23.

EXAMPLE 11

N-[2(S)-(2(R)-amino-3-mercaptopropylamino)-3(S)-methyl-pentyl]-N-methyl-D-norvalyl-homoserine lactone and N-[2(S)-(2(R)-amino-3-mercaptopropylamino)-3(S)-methyl-pentyl]-N-methyl-D-norvalyl-homoserine The title compounds were prepared according to the methods of Example 1, substituting D-norvaline methyl ester for isoleucyl benzyl ester, and isolated as its trifluoroacetate salt. $^1$H NMR (CD$_3$OD) δ4.49 (t, 1H, J=9Hz), 4.28–4.3 (m, 1H), 3.74–3.8 (m, 1H), 3.45–3.5 (m, 1H), 2.8–3.15 (m, 8H), 2.86 (s, 3H), 3.55–2.63 (m, 1H), 2.26–2.73 (m, 1H), 1.75–1.95 (m, 3H), 1.18–1.54 (m, 5H), 0.88–1.02 (m, 9H). Anal. calculated for C$_{19}$H$_{38}$N$_4$O$_3$S.3CF$_3$CO$_2$H.0.75 H$_2$O: C, 39.60; H, 5.65; N, 7.39; Found: C, 39.62; H, 6.03; N, 7.23.

The hydroxy acid was generated in situ according to Example 1, Step J.

EXAMPLE 12

3(S)-{N-[2(S)-(2(R)-amino-3-mercaptopropylamino)-3(S)-methylpentyl]-N-methyl-isoleucylamino}-6,6-dimethyl-tetrahydropyran-2-one and
2(S)-{N-[2(S)-(2(R)-amino-3-mercaptopropylamino)-3(S)-methylpentyl]-N-methyl-isoleucylamino}-5-methyl-5-hydroxyhexanoic acid

Step A: 2-N-(t-Butoxycarbonyl)amino-5-hydroxy-5-methylhexanoic acid

To a soln of N-(t-butoxycarbonyl)glutamic acid -5-methyl ester (2.52 g, 0.0096 mol) in THF (32 mL) was added methyl lithium (1.4M in ether) (30.2 mL, 0.042 mol) under argon with stirring at a rate to maintain the reaction temperature at <–60° C. After the addition the mixture was stirred at –70° C. for 1 h, then added to 10% citric acid soln (30 mL) and extracted with EtOAc (3×30 mL). The EtOAc layers were combined, washed with brine, and dried (Na$_2$SO$_4$). Filtration and concentration, followed by chromatography (SiO$_2$, CHCl$_3$: MeOH: HOAc, 90: 9:1) gave 1.2 g (48%) of the title compound as a yellow oil which solidified on standing. $^1$H NMR (CDCl$_3$) δ5.28 (br s, 1H), 4.35–4.43 (m, 1H), 1.75–2.0 (m, 2H), 1.58 (t, 2H, 9 Hz), 1.46 (s, 9H), 1.24 (s, 6H).

Step B: 3(S)-(t-Butoxycarbonyl)amino-6,6-dimethyl-tetrahydropyran- 2-one

2-N-(t-Butoxycarbonyl)amino-5-hydroxy-5-methylhexanoic acid (1.06 g, 4.05 mmol), dicyclohexyl-carbodiimide (DCC) (1.01 g, 4.86 mmol), and 4-dimethyl-aminopyridine (DMAP) (0.05 g, 0.4 mmol) were dissolved in CH$_2$Cl$_2$ (40 mL) with stirring at ambient temperature under argon. After 0.5 h the reaction mixture was filtered to remove dicylcohexylurea, the filtrate concentrated, then partitioned between EtOAc (100 mL) and 10% citric acid soln (50 mL). The organic layer was separated, washed with H$_2$O (3×50 mL), brine (1× 50 mL) and dried (Na$_2$SO$_4$). Filtration, concentration, and chromatography (SiO$_2$, EtOAc: hexane, 1:2) gave 0.6 g (61%)of the title compound as a white solid. $^1$H NMR (CDCl$_3$) δ5.33 (br s, 1H), 4.04–4.17 (m, 1H), 2.37–2.48 (m, 1H), 1.8–2.0 (m, 3H), 1.45 (s, 9H), 1.41 (s, 6H).

Step C: 3(S)-Amino-6,6-dimethyl-tetrahydropyran-2-one hydrochloride

3(S)-(t-Butoxycarbonyl)amino-6,6-dimethyl-tetrahydropyran- 2-one (0.36 g, 1.48 mmol) was dissolved in EtOAc (30 mL) and treated with HCl gas at –50° C. for 20 min and stirred at –30° to –50° C. for 20 min. Argon was bubbled into the soln for 10 min, then the soln was concentrated to give 0.265 g (100%) of the title compound as a white solid. $^1$H NMR (CD$_3$OD) δ4.05–4.15 (m, 1H), 2.2–2.32 (m, 1H), 2.0–2.15 (m, 3H), 1.48 (s, 3H), 1.43 (s, 3H).

Step D: 3(S)-{N-[2(S)-(2(R)-amino-3-mercaptopropyl-amino)-3(S)-methylpentyl]-N-methyl-isoleucyl-amino}-3-methyltetra-hydropyran- 2-one The title compound was prepared following the methods of Example 1, substituting 3(S)-amino-6,6-dimethyl-tetrahydropyran-2-one hydrochloride for homoserine lactone in Step E. The title compound was obtained as its trifluoroacetate salt. $^1$H NMR (CD$_3$OD) δ4.1–4.2 (m, 1H), 3.55 (d, 2H, J=6Hz), 3.0–3.3 (m, 6H), 2.90 (t, 2H, 6Hz), 2.81 (s, 3H), 2.28–2.39 (m, 1H), 1.82–2.15 (m, 5H), 1.55–1.6 (m, 1H), 1.53 (s, 3H), 1.45 (s, 3H), 1.2–1.4 (m, 2H), 0.92–1.04 (m, 12 H). Anal. calculated for C$_{23}$H$_{46}$N$_4$O$_3$S.3CF$_3$CO$_2$H.1.5 H$_2$O: C, 42.07; H, 6.33; N, 6.77; Found: C, 42.20; H, 6.10; N, 7.16.

The hydroxy acid was generated in situ according to Example 1, Step J.

EXAMPLE 13

3(S)-{N-[2(S)-(2(R)-amino-3-mercaptopropylamino)-3(S)-methylpentyl]-N-methyl-isoleucylamino}-3-methyltetrahydropyran- 2-one and
2(S)-{N-[2(S)-(2(R)-amino-3-mercaptopropylamino)-3(S)-methylpentyl]-N-methyl-isoleucylamino}-2-methyl-5-hydroxypentanoic acid

Step A: 2-Amino-2-methyl-5-hydroxypentanoic acid

Finely ground racemic a-methylglutamic acid (5.0 g, 0.029 tool) was suspended in THF (30 mL), treated with triethylborane (1M in THF, 32.32 mL, 0.032 mol), and heated at reflux for 36 h. After cooling to 0° C. the soln was treated dropwise with borane in THF (1M, 35.26 mL, 0.035 mol) and stirred at 0° C. for 3 h. The mixture was quenched with 5% aq HCl (30 mL), stirred for 0.5 h, concentrated on a rotary evaporator, and the residue dissolved in 5% HCl (44 mL) and heated at reflux for 0.75 h. After cooling and concentrating, the residue was taken up in MeOH (50 mL), concentrated, and this procedure repeated 3 × to give 5.69 g of the title compound which was not purified.

Step B: 2-(t-Butyloxycarbonyl)amino-2-methyl-5-hydroxypentanoic acid

2-Amino-2-methyl-5-hydroxypentanoic acid (5.69 g, 0.031 mol) was dissolved in 1,2-dimethoxy-ethane (DME) (60 mL)—H$_2$O (30 mL) with stirring at 0° C. The pH of the soln was adjusted to 9–10 with 1N NaOH soln, then di-t-butyl-dicarbonate (7.45 g, 0.034 mol) in DME (60mL)—H$_2$O (30 mL) was added dropwise while maintaining the mixture at a pH of 9–10 by concomitant addition of 1N NaOH soln. The reaction mixture was stirred at ambient temperature for 48 h with periodic addition of 1N NaOH to maintain the basic pH, then concentrated and partitioned between ether and H$_2$O. The aq layer was acidified with 10% citric acid soln, and extracted with EtOAC (3×50 mL). The organic layers were combined, washed with brine, and dried (Na$_2$SO$_4$). Filtration and concentration to dryness gave 3.0 g of crude title compound.

Step C: 3-(t-Butoxycarbonyl)amino-3-methyl-tetra-hydropyran-2-one 2-(t-Butyloxycarbonyl)amino-2-methyl-5-hydroxypentanoic acid (3.0 g, 0.012 mol) and EDC (2.56 g, 0.013 mol) were dissolved in DMF (20 mL) and stirred at ambient temperature for 18 h. The reaction mixture was concentrated to dryness, and the residue was partitioned between EtOAc (30 mL)–H$_2$O (30 mL), the organic layer separated, washed with brine and dried (Na$_2$SO$_4$). Filtration, concentration, and chromatography (SiO$_2$, EtOAc: hexane, 1:3) gave 0.86 g (31%) of the title compound. $^1$H NMR (CDCl$_3$) δ5.1 (br s, 1H), 4.35–4.55 (m, 2H), 2.49–2.64 (m, 1H), 1.78–2.1 (m, 3H), 1.45 (s, 3H), 1.41 (s, 9H).

Step D: 3-Amino-3-methyl-tetrahydropyran-2-one hydrochloride

The title compound was prepared as described in Example 12, Step C, and the resulting product used without further purification.

Step E: 3(S)-{N-[2(S)-(2(R)-amino-3-mercaptopropyl-amino)-3(S)-methylpentyl]-N-methyl-isoleucyl-amino}-3-methyl-tetrahydropyran- 2-one The title compound was prepared following the methods of Example 1, substituting 3-amino-3-methyl-tetrahydropyran-2-one hydrochloride for homoserine lactone in Step E. The title compound was obtained as its trifluoroacetate salt. $^1$H NMR (CD$_3$OD) δ4.42–4.55 (m, 2H), 3.48–3.6 (m, 2H), 3.17–3.28 (m, 1H), 2.88–3.15 (m, 5H), 2.79 (s, 3H), 2.3–2.45 (m, 1H), 1.97–2.18 (m, 2H), 1.82–11.98 (m, 3H), 1.6–1.73 (m, 1H), 1.56 (s, 3H), 1.21–1.5 (m, 4H), 0.86–1.05 (m, 12H). Anal. calculated for C$_{22}$H$_{44}$N$_4$O$_3$S.3CF$_3$CO$_2$H: C, 42.75; H, 6.02; N, 7.12; Found: C, 42.79; H, 6.18; N, 7.19.

The hydroxy acid was generated in situ according to Example 1, Step J.

EXAMPLE 14

N-[2(S)-(2(R)-amino-3-mercaptopropylamino)-3(S)-methylpentyl]-N- (1-naphthylmethyl)-glycyl methionine methyl ester and
N-[2(S)-(2(R)-amino-3-mercaptopropylamino)-3(S)-methylpentyl]-N-( 1-naphthylmethyl)-glycyl methionine

Step A: N-[2(S)-(2(R)-(t-butoxycarbonylamino-3-triphenylmethylmercaptopropylamino)-3(S)-methylpentyl]-N-( 1-naphthylmethyl)-glycyl methionine methyl ester N-[2(S)-(2(R)-(t-Butoxycarbonylamino-3-triphenylmethylmercaptopropylamino)- 3(S)-methylpentyl]-N-(1-naphthylmethyl)-glycyl methionine methyl ester was prepared following procedures outlined above in Example 1, Steps A–H. $^1$H NMR (CD$_3$OD) δ8.31 (d, 1H, J=9Hz), 7.72–7.89 (m, 2H), 7.16–7.6 (m, 19H), 4.35–4.46 (m, 1H), 4.08–4.2 (m, 2H), 3.59–3.78 (m, 1H), 3.63 (s, 3H), 3.05–3.25 (m, 2H), 2.03–2.78 (m, 7H), 1.95 (s, 3H), 1.48–1.79 (m, 3H), 1.41 (s, 9H), 1.09–1.38 (m, 4H), 0.75–0.93 (m, 6H).

Step B: N-[2(S)-(2(R)-amino-3-mercaptopropylamino)-3(S)-methylpentyl]-N-( 1-naphthylmethyl)-glycyl methionine methyl ester The title ester was obtained as its trifluoroacetate salt using the method described in Example 1, Step I. $^1$H NMR (CD$_3$OD) δ8.22 (d, 1H, J=9Hz), 7.95 (d, 1H, J=9Hz), 7.90 (d, 1H, J=9Hz), 7.45–7.67 (m, 4H), 4.55–4.62 (m, 1H), 4.40 (ABq, 2H), 3.69 (s, 3H), 3.57–3.72 (m, 3H), 3.04–3.22 (m, 3H), 2.78–2.97 (m, 3H), 2.36–2.62 (m, 3H), 2.05 (s, 3H), 2.01–2.17 (m, 1H), 1.81–1.96 (m, 1H), 1.63–1.75 (m, 1H), 1.1–1.28 (m, 2H), 0.87 (d, 3H, J=7 Hz), 0.81 (t, 3H, J=7 Hz). Anal. calculated for C$_{28}$H$_{44}$N$_4$O$_3$S$_2$. 2.75CF$_3$CO$_2$H: C, 46.65; H, 5.46; N, 6.50; Found: C, 46.77; H, 5.50; N, 6.69.

Step C: N-[2(S)-(2(R)-amino-3-mercaptopropylamino)-3(S)-methylpentyl]-N- (1-naphthylmethyl)-glycyl methionine The title acid was obtained as its trifluoroacetate salt using the method described in Example 6. $^1$H NMR (CD$_3$OD) δ8.25 (d, 1H, J=9Hz), 7.95 (d, 1H, J=9Hz), 7.90 (d, 1H, J=9Hz), 7.45–7.68 (m, 4H), 4.52–4.58 (m, 2H), 4.32 (d, 1H, J=13 Hz), 3.52–3.75 (m, 3H), 2.71–3.22 (m, 6H), 2.42–2.63 (m, 2H), 2.07 (s, 3H), 2.05–2.23 (m, 1H), 1.83–1.90 (m, 1H), 1.57–1.72 (m, 1H), 1.12–1.26 (m, 2H), 0.74–0.96 (m, 6H). Anal. calculated for C$_{27}$H$_{42}$N$_4$O$_3$S$_2$.2.5 CF$_3$CO$_2$H: C, 46.88; H, 5.47; N, 6.83; Found: C, 46.59; H, 5.50; N, 7.01.

The following compounds were prepared in a similar manner:

N-[2(S)-(2(R)-amino-3-mercaptopropylamino)-3(S)-methylpentyl]-N-( 1-naphthylmethyl)-glycyl methionine sulfone methyl ester Anal. calculated for C$_{28}$H$_{44}$N$_4$O$_5$S$_2$. 3CF$_3$CO$_2$H: C, 44.25; H, 5.13; N, 6.07; Found: C, 43.97; H, 5.14; N, 6.23.

N-[2(S)-(2(R)-amino-3-mercaptopropylamino)-3(S)-methylpentyl]-N-( 1-naphthylmethyl)-glycyl methionine sulfone Anal. calculated for C$_{27}$H$_{42}$N$_4$O$_5$S$_2$.2.75 CF$_3$CO$_2$H: C, 44.34; H, 5.12; N, 6.36; Found: C, 44.09; H, 5.13; N, 6.59.

N-[2(S)-(2(R)-amino-3-mercaptopropylamino)-3(S)-methylpentyl]-N-( 1-naphthylmethyl)-glycyl homoserine lactone Anal. calculated for C$_{26}$H$_{38}$N$_4$O$_3$S. 2.5 CF$_3$CO$_2$H: C, 48.24; H, 5.29; N, 7.26; Found: C, 48.21; H, 5.33; N, 7.49.

N-[2(S)-(2(R)-amino-3-mercaptopropylamino)-3(S)-methylpentyl]-N-benzyl-norvalyl methionine methyl ester m/e 541 (M+1)

N-[2(S)-(2(R)-amino-3-mercaptopropylamino)-3(S)-methylpentyl]-N-benzyl-norvalyl methionine Anal. calculated for C$_{26}$H$_{38}$N$_4$O$_3$S. 3 CF$_3$CO$_2$H: C, 44.24; H, 5.68; N, 6.45; Found: C, 44.10; H, 6.27; N, 6.82.

N-[2(S)-(2(R)-amino-3-mercaptopropylamino)-3(S)-methylpentyl]-N-benzyl-alanyl methionine methyl ester Anal. calculated for C$_{25}$H$_{44}$N$_4$O$_3$S2. 2.45 CF$_3$CO$_2$H: C, 45.33; H, 5.91; N, 7.07; Found: C, 45.28; H, 5.87; N, 7.20.

N-[2(S)-(2(R)-amino-3-mercaptopropylamino)-3(S)-methylpentyl]-N-benzyl-alanyl methionine Anal. calculated for C$_{24}$H$_{42}$N$_4$O$_3$S2. 2.25 CF$_3$CO$_2$H: C, 45.32; H, 5.91; N, 7.42; Found: C, 45.32; H, 5.98; N, 7.46.

N-[2(S)-(2(R)-amino-3-mercaptopropylamino)-3(S)-methylpentyl]-N-benzyl-glycyl methionine methyl ester Anal. calculated for $C_{24}H_{42}N_4O_3S_2$. 2 $CF_3CO_2H$. $H_2O$: C, 45.15; H, 6.23; N, 7.52; Found: C, 45.36; H, 5.86; N, 7.36.

N-[2(S)-(2(R)-amino-3-mercaptopropylamino)-3(S)-methylpentyl]-N-benzyl-glycyl methionine Anal. calculated for $C_{23}H_{40}N_4O_3S_2$. 2 $CF_3CO_2H$ .0.5 $H_2O$: C, 44.93; H, 6.01; N, 7.76; Found: C, 44.84; H, 5.76; N, 7.54.

N-[2(S)-(2(R)-amino-3-mercaptopropylamino)-3(S)-methylpentyl]-N-benzyl-glycyl methionine sulfone methyl ester Anal. calculated for $C_{24}H_{42}N_4O_5S_2$. 3 $CF_3CO_2H$ .1.5 $H_2O$: C, 40.04; H, 5.38; N, 6.23; Found: C, 39.73; H, 4.99; N, 6.31.

N-[2(S)-2(R)-amino-3-mercaptopropylamino)-3(S)-methylpentyl]-N-benzyl-glycyl methionine sulfone Anal. calculated for $C_{23}H_{40}N_4O_5S_2$. 4.1 $CF_3CO_2H$: C, 38.07; H, 4.52; N, 5.69; Found: C, 37.61; H, 4.62; N, 6.14.

N-[2(S)-(2(R)-amino-3-mercaptopropylamino)-3(S)-methylpentyl]-N-n-butyl-glycyl methionine m/e 451 (M+1)

N-[2(S)-(2(R)-amino-3-mercaptopropylamino)-3(S)-methylpentyl]-N-phenethyl-glycyl methionine methyl ester m/e 513 (M+1)

N-[2(S)-2(R)-amino-3-mercaptopropylamino)-3(S)-methylpentyl]-N-phenethyl-glycyl methionine Anal. calculated for $C_{24}H_{42}N_4O_3S_2$. 3 $CF_3CO_2H$. $2H_2O$: C, 44.08; H, 6.34; N, 7.35; Found: C, 43.69; H, 6.34; N, 7.21.

N-[2(S)-(2(R)-amino-3-mercaptopropylamino)-3(S)-methylpentyl]-N-benzyl-phenylalanyl methionine Anal. calculated for $C_{30}H_{46}N_4O_3S_2$.2.5 $CF_3CO_2H$: C, 48.88; H, 5.69; N, 6.52; Found: C, 49.14; H, 5.87; N, 6.65.

N-[2(S)-(2(R)-amino-3-mercaptopropylamino)-3(S)-methylpentyl]-N-( 1-naphthylmethyl)-norvalyl methionine Anal. calculated for $C_{30}H_{48}N_4O_3S_2$.2.2 $CF_3CO_2H$: C, 49.89; H, 6.11; N, 6.77; Found: C, 49.86; H, 6.15; N, 6.97.

N-[2(S)-(2(R)-amino-3-mercaptopropylamino)-3(S)-methylpentyl]-N-( 1-naphthylmethyl)-norvalyl methionine methyl ester Anal. calculated for $C_{31}H_{50}N_4O_3S_2$.2.5 $CF_3CO_2H$: C, 49.30; H, 6.03; N, 6.47; Found: C, 49.26; H, 6.09; N, 6.39.

N-[2(S)-(2(R)-amino-3-mercaptopropylamino)-3(S)-methylpentyl]-N-benzyl-D-alanyl methionine Anal. calculated for $C_{24}H_{42}N_4O_3S_2$.2.25 $CF_3CO_2H$: C, 45.32; H, 5.91; N, 7.42; Found: C, 45.28; H, 5.89; N, 7.48.

N-[2(S)-(2(R)-amino-3-mercaptopropylamino)-3(S)-methylpentyl]-N-benzyl-D-alanyl methionine methyl ester Anal. calculated for $C_{25}H_{44}N_4O_3S_2$. 2.25 $CF_3CO_2H$: C, 46.05; H, 6.06; N, 7.28; Found: C, 46.04; H, 6.07; N, 7.29.

N-[2(R)-(2(R)-amino-3-mercaptopropylamino)-3(S)-methylpentyl]-N-benzyl-D-alanyl methionine Anal. calculated for $C_{24}H_{42}N_4O_3S_2$.2.1 $CF_3CO_2H$: C, 45.88; H, 6.02; N, 7.59; Found: C, 45.75; H, 6.10; N, 7.62.

N-[2(R)-(2(R)-amino-3-mercaptopropylamino)-3(S)-methylpentyl]-N-benzyl-D-alanyl methionine methyl ester Anal. calculated for $C_{25}H_{44}N_4O_3S_2$. 2.35 $CF_3CO_2H$: C, 45.69; H, 5.98; N, 7.18; Found: C, 45.61; H, 6.11; N, 7.15.

N-[2(R)-(2(R)-amino-3-mercaptopropylamino)-3(S)-methylpentyl]-N-benzyl-alanyl methionine Anal. calculated for $C_{24}H_{42}N_4O_3S_2$.2.3 $CF_3CO_2H$: C, 45.14; H, 5.87; N, 7.36; Found: C, 45.15; H, 5.96; N, 7.41.

N-[2(R)-(2(R)-amino-3-mercaptopropylamino)-3(S)-methylpentyl]-N-benzyl-alanyl methionine methyl ester Anal. calculated for $C_{25}H_{44}N_4O_3S_2$.2.4 $CF_3CO_2H$: C, 45.51; H, 5.95; N, 7.12; Found: C, 45.51; H, 6.03; N, 7.33.

N-[2(S)-(2(R)-amino-3-mercaptopropylamino)-3(S)-methylpentyl]-N-( 3-quinolylmethyl)-glycyl methionine Anal. calculated for $C_{26}H_{41}N_5O_3S_2$. 3 $CF_3CO_2H$. 1.5 $H_2O$: C, 42.47; H, 5.24; N, 7.74; Found: C, 42.30; H, 5.10; N, 7.70.

N-[2(S)-(2(R)-amino-3-mercaptopropylamino)-3(S)-methylpentyl]-N-( 3-quinolylmethyl)-glycyl methionine methyl ester Anal. calculated for $C_{27}H_{43}N_5O_3S_2$. 3.85 $CF_3CO_2H$: C, 42.15; H, 4.78; N, 7.08; Found: C, 41.96; H, 5.01; N, 7.48.

EXAMPLE 15

N-[2(S)-(2(R)-amino-3-mercaptopropylamino)-3(S)-methylpentyl]-N-benzoyl-norvalyl methionine and
N-[2(S)-(2(R)-amino-3-mercaptopropylamino)-3(S)-methylpentyl]-N-benzoyl-norvalyl methionine methyl ester The title compounds were prepared according to the methods of Examples 1 and 2, substituting norvaline-methionine methyl ester for isoleucine benzyl ester in Step B and using the following step for Steps C, D and E of Example 1 combined.

Step C.
N-[2(S)-(t-butoxycarbonylamino)-3(S)-methylpentyl]-N-benzoyl-norvaline methionine methyl ester Benzoyl chloride (0.11 mL, 0.87 mmol) was added to a solution of N-[2(S)-(t-Butoxycarbonylamino)-3(S)-methylpentyl]-norvaline-methionine methyl ester (0.20 g, 0.43 mmol) and $Et_3N$ (0.12 mL, 0.87 mmol) in $CH_2Cl_2$ (5 mL) with cooling at 0° C. with stirring. After 0.5 h, the mixture was concentrated and partitioned between EtOAc and $H_2O$, the organic layer separated, washed with 1N NaOH solution, $H_2O$, brine, and dried ($Na_2SO_4$). Filtration and concentration gave TITLE after chromatography ($SiO_2$, Hexane: EtOAc, 3:1 to 1:1).

N-[2(S)-(2(R)-amino-3-mercaptopropylamino)-3(S)-methylpentyl]-N-benzoyl-norvalyl methionine methyl ester Anal. calculated for $C_{27}H_{46}N_4O_4S_2$. 2 $CF_3CO_2H$ 1 $H_2O$: C, 46.49; H, 6.29; N, 7.00; Found: C, 46.15; H, 5.90; N, 6.81.

N-[2(S)-(2(R)-amino-3-mercaptopropylamino)-3(S)-methylpentyl-N-benzoyl-norvalyl methionine Anal. calculated for $C_{26}H_{44}N_4O_4S_2$. 2 $CF_3CO_2H$. 1 $H_2O$: C, 45.79; H, 6.15; N, 7.12; Found: C, 45.79; H, 5.84; N, 7.29

EXAMPLE 16

N-[2(S)-(2(R)-amino-3-mercaptopropyl (methylamino))-3(S)-methylpentyl]-N-(1-naphthylmethyl)-glycyl methionine methyl ester and N-[2(S)-(2(R)-amino-3-mercaptopropyl (methylamino))-3(S)-methylpentyl]-N-(1-naphthylmethyl)-glycyl methionine Step A: N-[2(S)-(2(R)-(t-butoxycarbonylamino-3-triphenylmethylmercaptopropyl(methylamino))-3(S)-methylpentyl]-N-( 1-naphthylmethyl)-glycyl methionine methyl ester N-[2(S)-(2(R)-(t-Butoxycarbonylamino-3-triphenylmethylmercaptopropylamino)- 3(S)-methylpentyl]-N-(1-naphthylmethyl)-glycyl methionine methyl ester (Example 14, Step A) (0.18 g, 0.2 mmol) was dissolved in MeOH (5 mL) and treated with acetic acid (0.0117 mL, 0.2 mmol), formaldehyde (37% aqueous solution) (0.030 mL, 0.4 mmol) and sodium cyanoborohydride (0.019 g, 0.3 mmol) and stirred at ambient temperature for 18 h. The reaction mixture was concentrated, and the residue partitioned between EtOAc and aq satd $NaHCO_3$ solution, the organic layer separated, washed with brine, dried (Na₂SO₄). Filtration and concentration gave the title compound after chromatography (SiO₂, CH₂Cl₂:MeOH, 98:2). $^1$H NMR (CD₃OD) δ8.31(d, 1H, J=9Hz), 7.75–7.89 (m, 2H), 7.15–7.5 (m, 19H), 4.25–4.40 (m, 2H), 4.03 (d, 1H, J=12 Hz), 3.5–3.7 (m, 1H), 3.66 (s, 3H), 3.2–3.4 (m, 3H), 2.78–2.9 (m, 1H), 2.45–2.66 (m, 3H), 2.2–2.4 (m, 3H), 2.05 (s, 3H), 1.95 (s, 3H), 1.95–2.2 (m, 2H), 1.75–1.9 (m, 1H), 1.3–1.6 (m, 2H), 1.36 (s, 9H), 0.95–1.1 (m, 1H), 0.75–0.93 (m, 6H).

Step B: N-[2(S)-(2(R)-amino-3-mercaptopropyl (methylamino))-3(S)-methylpentyl]-N-(1-naphthylmethyl)-glycyl methionine methyl ester The title ester was obtained as its trifluoroacetate salt using the method described in Example 1, Step I. $^1$H NMR (CD₃OD) δ8.29 (d, 1H, J=9Hz), 8.0 (d, 2H, J=9Hz), 7.5–7.75 (m, 4H), 4.6–4.8 (m, 2H), 4.2–4.4 (m, 1H), 3.74 (s, 3H), 3.6–4.0 (m, 3H), 2.95–3.4 (m, 3H), 2.5–2.85 (m, 8H), 2.08 (s, 3H), 1.92–2.23 (m, 2H), 1.6–1.9 (m, 2H), 1.1–1.36 (m, 2H), 0.78–0.92 (m, 6H). m/e 563 (M+1)

Step C: N-[2(S)-(2(R)-amino-3-mercaptopropyl(methylamino))-3(S)-methylpentyl]-N-(1-naphthylmethyl)-glycyl methionine The title acid was obtained as its trifluoroacetate salt using the method described in Example 6. $^1$H NMR (CD₃OD) δ8.3 (d, 1H, J=9Hz), 7.99 (d, 2H, J=9Hz), 7.5–7.65 (m, 4H), 4.48–4.8 (m, 2H), 4.2–4.36 (m, 1H), 3.55–3.95 (m, 2H), 2.82–3.55 (m, 3H), 2.45–2.82 (m, 8H), 2.10 (s, 3H), 2.14–2.28 (m, 1H), 1.6–2.1 (m, 4H), 1.08–1.35 (m, 2H), 0.75–0.9 (m, 6H). Anal. calculated for C₂₈H₄₄N₄O₃S₂.2.75 CF₃CO₂H: C, 46.65; H, 5.46; N, 6.50; Found: C, 46.93; H, 5.75; N, 6.86.

EXAMPLE 17

N-[2(S)-(2(R)-amino-3-mercaptopropylamino)-3(S)-methylpentyl]-N-[1-(5-dimethylamino)naphthylmethylsulfonyl]-glycyl methionine and
N-[2(S)-(2(R)-amino-3-mercaptopropylamino)-3(S)-methylpentyl]-N-[1-(5-dimethylamino)naphthylmethylsulfonyl]-glycyl methionine methyl ester Using the methods described in Example 1, but using glycine methyl ester instead of isoleucine benzyl ester in Step B, and substituting the following step for Step C., the title compounds were prepared.

Step C. N-[(2S)-t-Butoxycarbonylamino)-3(S)-methyl-pentyl]-N-[1-(5-dimethylamino)naphthylmethylsulfonyl]-glycine methyl ester Dansyl chloride (0.337 g, 1.25 mmol) was added to a solution of N-[( 2S)-t-Butoxycarbonylamino)-3(S)-methylpentyl]-glycine methyl ester (0.30 g, 1.04 mmol) and diisopropylethylamine (0.218 mL, 1.25 mmol) in CH₂Cl₂ (5 mL) with stirring at 0° C. in an ice-H₂O bath. After stirring for 18 h at ambient temperature, the reaction mixture was partitioned between EtOAc and H₂O, the organic layer separated, washed with NaHCO₃ solution, brine, and dried (Na₂SO₄). Filtration and concentration gave the title compound after chromatography (SiO₂, EtOAc: hexane, 1:6 to 1:3). $^1$H NMR (CDCl₃) δ8.54 (d, 1H, J=9Hz), 8.27–8.33(m, 2H), 7.5–7.57 (m, 2H), 7.19 (d, 1H, J=7.5 Hz), 4.65 (br d, 1H, J=9Hz), 4.42 (d, 1H, J=18 Hz), 4.15 (d, 1H, J=18 Hz), 3.67–3.78 (m, 1H), 3.49 (s, 3H), 3.43–3.6 (m, 2H), 2.89 (s, 6H), 1.44 (s, 9H), 1.3–1.64 (m, 2H), 0.95–1.1 (m, 1H), 0.82–0.93 (m, 6H).

N-[2(S)-(2(R)-amino-3-mercaptopropylamino)-3(S)-methylpentyl]-N-[1-( 5-dimethylamino)naphthylmethylsulfonyl]-glycyl methionine methyl ester Anal. calculated for C₂₉H₄₇N₅O₅S₃.3 CF₃CO₂H: C, 42.72; H, 5.12; N, 7.12; Found: C, 42.58; H, 5.18; N, 6.76.

N-[2(S)-(2(R)-amino-3-mercaptopropylamino)-3(S)-methylpentyl]-N-[1-( 5-dimethylamino)naphthylmethylsulfonyl]-glycyl methionine Anal. calculated for C₂₈H₄₅N₅O₅S₃.3.75 CF₃CO₂H: C, 40.39; H, 4.66; N, 6.64; Found: C, 40.34; H, 4.90; N, 6.99.

EXAMPLE 18

In vitro inhibition of ras farnesyl transferase

Assays of farnesyl-protein transferase. Partially purified bovine FPTase and Ras peptides (Ras-CVLS, Ras-CVIM and RAS-CAIL) were prepared as described by Schaber et al., *J. Biol. Chem.* 265:14701–14704 (1990), Pompliano, et al., *Biochemistry* 31:3800 (1992) and Gibbs et at., *PNAS U.S.A.* 86:6630–6634 (1989), respectively. Bovine FPTase was assayed in a volume of 100 μl containing 100 mM N-(2-hydroxy ethyl) piperazine-N'-(2-ethane sulfonic acid) (HEPES), pH 7.4, 5 mM MgCl₂, 5 mM dithiothreitol (DTT), 100 mM [³H]-farnesyl diphosphate ([³H]-FPP; 740 CBq/mmol, New England Nuclear), 650 nM Ras-CVLS and 10 μg/ml FPTase at 31° C. for 60 min. Reactions were initiated with FPTase and stopped with 1 ml of 1.0M HCL in ethanol. Precipitates were collected onto filter-mats using a TomTec Mach II cell harvestor, washed with 100% ethanol, dried and counted in an LKB β-plate counter. The assay was linear with respect to both substrates, FPTase levels and time; less than 10% of the [³H]-FPP was utilized during the reaction period. Purified compounds were dissolved in 100% dimethyl sulfoxide (DMSO) and were diluted 20-fold into the assay. Percentage inhibition is measured by the amount of incorporation of farnesyl in the presence of the test compound when compared to the amount of incorporation in the absence of the test compound.

Human FPTase was prepared as described by Omer et at., *Biochemistry* 32:5167–5176 (1993). Human FPTase activity was assayed as described above with the exception that 0.1% (w/v) polyethylene glycol 20,000, 10 μM ZnCl₂ and 100 nM Ras-CVIM were added to the reaction mixture. Reactions were performed for 30 min., s stopped with 100 μl of 30% (v/v) trichloroacetic acid (TCA) in ethanol and processed as described above for the bovine enzyme.

The compounds of the instant invention were tested for inhibitory activity against human or bovine FPTase by the assay described above and were found to have IC₅₀ of < 10 μM. Examples of such activity are shown in Table 1.

TABLE 1

| Inhibition of RAS farnesylation by compounds of this invention | |
|---|---|
| Compound | IC₅₀ (nM) |
| N-[2(S)-2(R)-amino-3-mercaptopropyl-amino)-3(S)-methylpentyl]-N-methyl-isoleucyl-homoserine | 72 (Bovine) |
| N-[2(S)-2(R)-amino-3-mercaptopropyl- | 20 |

TABLE 1-continued

Inhibition of RAS farnesylation by compounds of this invention

| Compound | IC$_{50}$ (nM) |
| --- | --- |
| amino)-3(S)-methylpentyl]-N-methyl-isoleucyl-methionine | (Recombinant Human) |

*(IC$_{50}$ is the concentration of the test compound which gives 50% inhibition of FTase under the described assay conditions)

EXAMPLE 19

In vivo ras farnesylation assay

The cell line used in this assay was the v-ras line, which expressed viral Ha-ras p21. The assay was performed essentially as described in DeClue, J. E. et. al., Cancer Research 51:712–717, (1991). Cells in 10 cm dishes at 50–75% confluency were treated with the test s compound (final concentration of solvent, methanol or dimethyl sulfoxide, was 0.1%). After 4 hours at 37° C., the cells were labelled in 3 ml methionine-free DMEM supplemented with 10% regular DMEM, 2% fetal bovine serum and 400 μCi[$^{35}$S] methionine (1000 Ci/mmol). After an additional 20 hours, the cells were lysed in 1 ml lysis buffer (1% NP40/20 mM HEPES, pH 7.5/5 mM MgCl$_2$/1 mM DTT/10 μg/ml aprotinen/2 μg/ml leupeptin/2 μg/ml antipain/0.5 mM PMSF) and the lysates cleared by centrifugation at 100,000 × g for 45 min. Aliqouts of lysates containing equal numbers of acid-precipitable counts were bought to 1 ml with IP buffer (lysis buffer lacking DTT) and immunoprecipitated with the ras-specific monoclonal antibody Y13-259 (Furth, M. E. et. al., J. Virol. 43:294–304, (1982)). Following a 2 hour antibody incubation at 4° C., 200 ml of a 25% suspension of protein A-Sepharose coated with rabbit anti rat IgG was added for 45 min. The immunoprecipitates were washed four times with IP was buffer (20 nM HEPES, pH 7.5/1 mM EDTA/1% Triton X-100.0.5% deoxycholate/0.1%/SDS/0.1M NaCl) boiled in SDS-PAGE sample buffer and loaded on 13% acrylamide gels. When the dye front reached the bottom, the gel was fixed, soaked in Enlightening, dried and autoradiographed. The intensities of the bands corresponding to farnesylated and nonfarnesylated ras proteins were compared to determine the percent inhibition of farnesyl transfer to protein. Data for representative test compounds are tabulated in Table 2.

TABLE 2

Inhibition of Ras farnesylation by the compounds of this invention in the v-ras cell line

| Compound | IC$_{50}$ (μM) |
| --- | --- |
| N-[2(S)-2(R)-amino-3-mercaptopropyl-amino)-3(S)-methylpentyl]-N-methyl-isoleucyl-homoserine lactone | 50 |
| N-[2(S)-2(R)-amino-3-mercaptopropyl-amino)-3(S)-methylpentyl]-N-methyl-isoleucyl-methionine methyl ester | 5 |

What is claimed is:

1. A compound which inhibits farnesyl-protein transferase of the formula I:

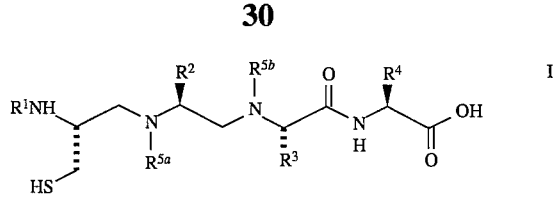

wherein:

R$^1$ and R$^{5a}$ are independently selected from:
  hydrogen, a C$_1$–C$_6$ alkyl group, a C$_1$–C$_6$ acyl group, an aroyl group, a C$_1$–C$_6$ alkylsulfonyl group, C$_1$–C$_6$ aralkylsulfonyl group or arylsulfonyl group wherein the alkyl group and acyl group is optionally substituted with substituted or unsubstituted aryl or heterocycle;

R$^2$, R$^3$ and R$^4$ are independently selected from:
  a) a side chain of naturally occurring amino acids,
  b) an oxidized form of a side chain of naturally occurring amino acids selected from methionine sulfoxide and methionine sulfone,
  c) substituted or unsubstituted C$_1$–C$_8$ alkyl, C$_3$–C$_8$ cycloalkyl, C$_2$–C$_8$ alkenyl, aryl or heterocycle groups, wherein the aliphatic substituent is optionally substituted with an aryl, heterocycle or C$_3$–C$_8$ cycloalkyl;

R$^{5b}$ is a C$_1$–C$_6$ alkyl group, a C$_1$–C$_6$ acyl group, an aroyl group, a C$_1$–C$_6$ alkylsulfonyl group, C$_1$–C$_6$ aralkylsulfonyl group or arylsulfonyl group wherein the alkyl group and acyl group is optionally substituted with substituted or unsubstituted aryl or heterocycle;

and the pharmaceutically acceptable salts thereof.

2. A prodrug of a compound of claim 1 of the formula II:

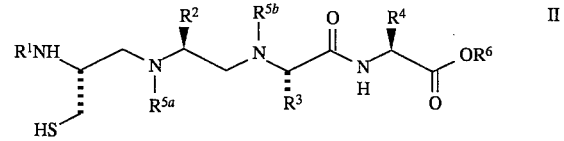

wherein:

R$^1$ and R$^{5a}$ are independently selected from:
  hydrogen, a C$_1$–C$_6$ alkyl group, a C$_1$–C$_6$ acyl group, an aroyl group, a C$_1$–C$_6$ alkylsulfonyl group, C$_1$–C$_6$ aralkylsulfonyl group or arylsulfonyl group wherein the alkyl group and acyl group is optionally substituted with substituted or unsubstituted aryl or heterocycle;

R$^2$, R$^3$ and R$^4$ are independently selected from:
  a) a side chain of naturally occurring amino acids,
  b) an oxidized form of a side chain of naturally occurring amino acids selected from methionine sulfoxide and methionine sulfone,
  c) substituted or unsubstituted C$_1$–C$_8$ alkyl, C$_3$–C$_8$ cycloalkyl, C$_2$–C$_8$ alkenyl, aryl or heterocycle groups, wherein the aliphatic substituent is optionally substituted with an aryl, heterocycle or C$_3$–C$_8$ cycloalkyl;

R$^{5b}$ is a C$_1$–C$_6$ alkyl group, a C$_1$–C$_6$ acyl group, an aroyl group, a C$_1$–C$_6$ alkylsulfonyl group, C$_1$–C$_6$ aralkylsulfonyl group or arylsulfonyl group wherein the alkyl group and acyl group is optionally substituted with substituted or unsubstituted aryl or heterocycle;

R$^6$ is a substituted or unsubstituted aliphatic, aryl or heterocyclic group, wherein the aliphatic substituent is optionally substituted with an aryl or heterocyclic ring;

and the pharmaceutically acceptable salts and disulfides thereof.

3. A compound which inhibits farnesyl-protein transferase of the formula III:

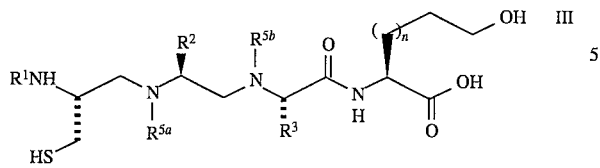

wherein:
R¹ and R⁵ᵃ are independently selected from:
hydrogen, a $C_1$–$C_6$ alkyl group, a $C_1$–$C_6$ acyl group, an aroyl group, a $C_1$–$C_6$ alkylsulfonyl group, $C_1$–$C_6$ aralkylsulfonyl group or arylsulfonyl group wherein the alkyl group and acyl group is optionally substituted with substituted or unsubstituted aryl or heterocycle;

R² and R³ are independently selected from:
a) a side chain of naturally occurring amino adds,
b) an oxidized form of a side chain of naturally occurring amino acids selected from methionine sulfoxide and methionine sulfone,
c) substituted or unsubstituted $C_1$–$C_8$ alkyl, $C_3$–$C_8$ cycloalkyl, $C_2$–$C_8$ alkenyl, aryl or heterocycle groups, wherein the aliphatic substituent is optionally substituted with an aryl, heterocycle or $C_3$–$C_8$ cycloalkyl;

R⁵ᵇ is a $C_1$–$C_6$ alkyl group, a $C_1$–$C_6$ acyl group, an aroyl group, a $C_1$–$C_6$ alkylsulfonyl group, $C_1$–$C_6$ aralkylsulfonyl group or arylsulfonyl group wherein the alkyl group and acyl group is optionally substituted with substituted or unsubstituted aryl or heterocycle;

n is 1 or 2;
and the pharmaceutically acceptable salts thereof.

4. A compound which inhibits farnesyl-protein transferase which is:
N-[2(S)-(2(R)-amino-3-mercaptopropylamino)-3(S)-methylpentyl]-N-methyl-isoleucyl-homoserine,
N-[2(S)-(2(R)-amino-3-mercaptopropylamino)-3(S)-methylpentyl]-N-methyl-phenylalanyl-homoserine,
N-[2(S) -(2(R)-amino-3-mercaptopropylamino)-3-methylbutyl]-N-methyl-phenylalanyl-homoserine,
2(S)-{N- [2(S)-(2(R)-amino-3-mercaptopropylamino)-3(S)-methylpentyl]-N-methyl-isoleucylamino}- 2-methyl-5-hydroxypentanoic acid,
2(S)-{N-[2(S)-(2(R)-amino-3-mercaptopropylamino)-3(S)-methylpentyl]-N-methyl-isoleucylamino}- 5-methyl-5-hydroxyhexanoic acid,
N-[2(S)-(2(R)-amino-3-mercaptopropylamino)-3(S)-methylpentyl]-N-methyl-norvalyl-homoserine,
N-[2(S)-(2(R)-amino-3-mercaptopropylamino)-3(S)-methylpentyl]-N-methyl-isoleucyl-methionine,
N-[2(S)-(2(R)-amino-3-mercaptopropylamino)-3(S)-methylpentyl]-N-methyl-phenylalanyl-methionine,
N-[2(S)-(2(R)-amino-3-mercaptopropylamino)-3(S)-methylpentyl]-N-methyl-norvalyl-methionine,
N-[2(S)-(2(R)-amino-3-mercaptopropylamino)-3(S)-methylpentyl]-N-methyl-D-norvalyl-homoserine,
N-[2(S)-(2(R)-amino-3-mercaptopropylamino)-3(S)-methylpentyl]-N-(1-naphthylmethyl)-glycyl methionine,
N-[2(S)-(2(R)-amino-3-mercaptopropylamino)-3(S)-methylpentyl]-N-( 1-naphthylmethyl)-glycyl methionine sulfone,
N-[2(S)-(2(R)-amino-3-mercaptopropylamino)-3(S)-methylpentyl]-N-( 1-naphthylmethyl)-glycyl homoserine,
N-[2(S)-(2(R)-amino-3-mercaptopropylamino)-3(S)-methylpentyl]-N-benzyl-norvalyl methionine,
N-[2(S)-(2(R)-amino-3-mercaptopropylamino)-3(S)-methylpentyl]-N-benzyl-alanyl methionine,
N-[2(S)-(2(R)-amino-3-mercaptopropylamino)-3(S)-methylpentyl]-N-benzyl-glycyl methionine,
N-[2(S)-(2(R)-amino-3-mercaptopropylamino)-3(S)-methylpentyl]-N-benzyl-glycyl methionine sulfone,
N-[2(S)-(2(R)-amino-3-mercaptopropylamino)-3(S)-methylpentyl]-N-n-butyl-glycyl methionine,
N-[2(S)-(2(R)-amino-3-mercaptopropylamino)-3(S)-methylpentyl]-N-phenethyl-glycyl methionine,
N-[2(S)-(2(R)-amino-3-mercaptopropylamino)-3(S)-methylpentyl]-N-benzyl-phenylalanyl methionine,
N-[2(S)-(2(R)-amino-3-mercaptopropylamino)-3(S)-methylpentyl]-N-benzyl-D-alanyl methionine,
N-[2(R)-(2(R)-amino-3-mercaptopropylamino)-3(S)-methylpentyl]-N-benzyl-D-alanyl methionine,
N-[2(R)-(2(R)-amino-3-mercaptopropylamino)-3(S)-methylpentyl]-N-benzyl-alanyl methionine,
N-[2(S)-(2(R)-amino-3-mercaptopropylamino)-3(S)-methylpentyl]-N-(3-quinolylmethyl)-glycyl methionine,
N-[2(S)-(2(R)-amino-3-mercaptopropylamino)-3(S)-methylpentyl]-N-benzoyl-norvalyl methionine,
N-[2(S)-(2(R)-amino-3-mercaptopropyl(methylamino))-3(S)-methylpentyl]-N-( 1-naphthylmethyl)-glycyl methionine, or
N-[2(S)-(2(R)-amino-3-mercaptopropylamino)-3(S)-methylpentyl]-N-[1-(5-dimethylamino)naphthylmethylsulfonyl]-glycyl methionine,
and the pharmaceutically acceptable salts thereof.

5. A prodrug of a compound which inhibits farnesyl-protein transferase which is:
N-[2(S)-(2(R)-amino-3-mercaptopropylamino)-3(S)-methylpentyl]-N-methyl-isoleucyl-methionine methyl ester,
N-[2(S)-(2(R)-amino-3-mercaptopropylamino)-3(S)-methylpentyl]-N-methyl-phenylalanyl-methionine methyl ester,
N-[2(S)-(2(R)-amino-3-mercaptopropylamino)-3(S)-methylpentyl]-N-methyl-norvalyl-methionine methyl ester,
N-[2(S)-(2(R)-amino-3-mercaptopropylamino)-3(S)-methylpentyl]-N-( 1-naphthylmethyl)-glycyl methionine methyl ester,
N-[2(S)-(2(R)-amino-3-mercaptopropylamino)-3(S)-methylpentyl]-N-( 1-naphthylmethyl)-glycyl methionine sulfone methyl ester,
N-[2(S)-(2(R)-amino-3-mercaptopropylamino)-3(S)-methylpentyl]-N-benzyl-norvalyl methionine methyl ester,
N-[2(S)-(2(R)-amino-3-mercaptopropylamino)-3(S)-methylpentyl]-N-benzyl-alanyl methionine methyl ester,
N-[2(S)-(2(R)-amino-3-mercaptopropylamino)-3(S)-methylpentyl]-N-benzyl-glycyl methionine methyl ester,
N-[2(S)-(2(R)-amino-3-mercaptopropylamino)-3(S)-methylpentyl]-N-benzyl-glycyl methionine sulfone methyl ester,
N-[2(S)-(2(R)-amino-3-mercaptopropylamino)-3(S)-methylpentyl]-N-phenethyl-glycyl methionine methyl ester,
N-[2(S)-(2(R)-amino-3-mercaptopropylamino)-3(S)-methylpentyl]-N-( 1-naphthylmethyl)-norvalyl methionine methyl ester,
N-[2(S)-(2(R)-amino-3-mercaptopropylamino)-3(S)-methylpentyl]-N-benzyl-D-alanyl methionine methyl ester,
N-[2(R)-(2(R)-amino-3-mercaptopropylamino)-3(S)-methylpentyl]-N-benzyl-D-alanyl methionine methyl ester,
N-[2(R)-(2(R)-amino-3-mercaptopropylamino)-3(S)-methylpentyl]-N-benzyl-alanyl methionine methyl ester,
N-[2(S)-(2(R)-amino-3-mercaptopropylamino)-3(S)-methylpentyl]-N-( 3-quinolylmethyl)-glycyl methionine methyl ester, N-[2(S)-(2(R)-amino-3-mercaptopropylamino)-3(S)-methylpentyl]-N-benzoyl-norvalyl methionine methyl ester, N-[2(S)-(2(R)-amino-3-mercaptopropyl(methylamino))-3(S)-methylpentyl]-N-( 1-naphthylmethyl)-glycyl methionine methyl ester, or N-[2(S)-(2(R)-amino-3-mercaptopropylamino)-3(S)-methylpentyl]-N-[1-(5-dimethylamino)naphthylmethylsulfonyl]-glycyl methionine methyl ester, and the pharmaceutically acceptable salts and disulfides thereof.

6. The compound of claim 3 which is:

N-[2(S)-(2(R)-amino-3-mercaptopropylamino)-3(S)-methylpentyl]-N-methyl-isoleucyl-homoserine

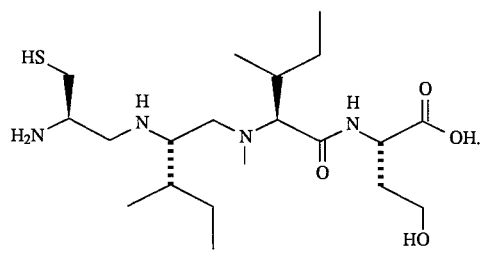

7. The compound of claim 1 which is:

N-[2(S)-2(R)-amino-3-mercaptopropylamino)-3(S)-methylpentyl]-N-methyl-isoleucyl-methionine

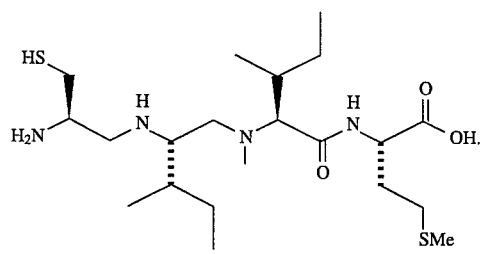

8. The compound of claim 2 which is:

N-[2(S)-2(R)-amino-3-mercaptopropylamino)-3(S)-methylpentyl]-N-methyl-isoleucyl-methionine methyl ester

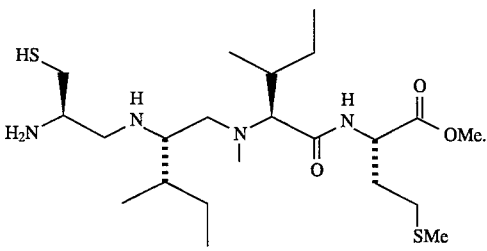

9. The compound of claim 1 which is:

N-[2(S)-(2(R)-amino-3-mercaptopropylamino)-3(S)-methylpentyl]-N-( 1-naphthylmethyl)-glycyl-methionine

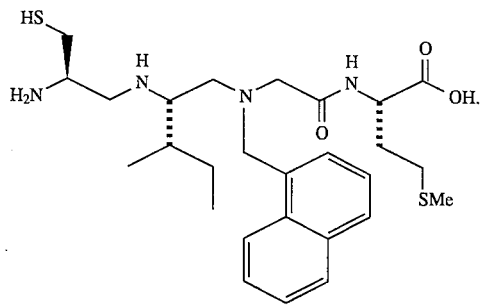

10. The compound of claim 2 which is:

N-[2(S)-(2(R)-amino-3-mercaptopropylamino)-3(S)-methylpentyl]-N-( 1-naphthylmethyl)-glycyl-methionine methyl ester

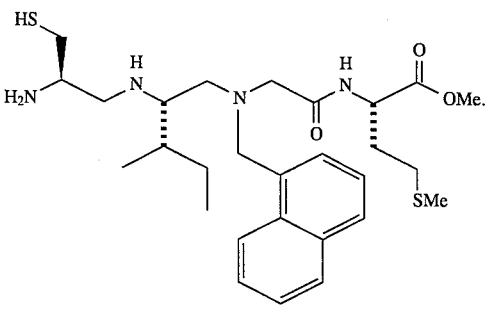

11. The compound of claim 1 which is:

N-[2(S)-(2(R)-amino-3-mercaptopropylamino)-3(S)-methylpentyl]-N-( 1-naphthylmethyl)-glycyl-methionine sulfone

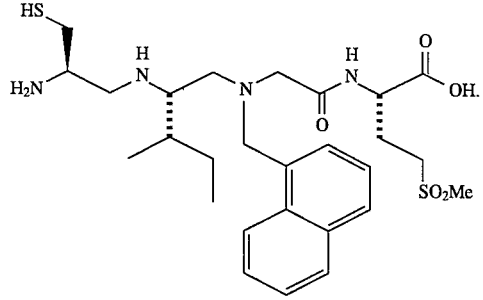

12. The compound of claim 2 which is:

N-[2(S)-(2(R)-amino-3-mercaptopropylamino)-3(S)-methylpentyl]-N-( 1-naphthylmethyl)-glycyl-methionine sulfone methyl ester

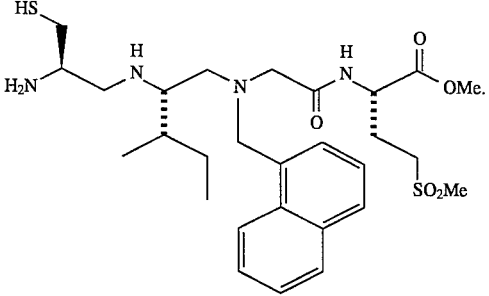

13. The compound of claim 1 which is:

N-[2(S)-(2(R)-amino-3-mercaptopropylamino)-3(S)-methylpentyl]-N-benzyl-glycyl-methionine

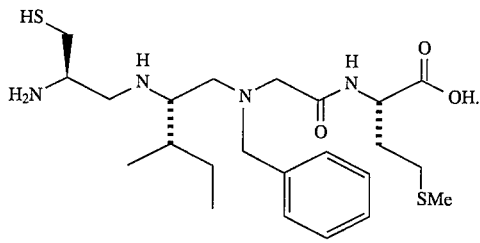

14. The compound of claim 2 which is:

N-[2(S)-(2(R)-amino-3-mercaptopropylamino)-3(S)-methylpentyl]-N-benzyl-glycyl-methionine methyl ester

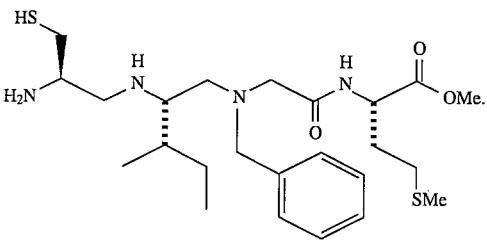

15. A pharmaceutical composition comprising a pharmaceutical carrier, and dispersed therein, a therapeutically effective amount of a compound of claim 2.

16. A method for inhibiting farnesylation of Ras protein which comprises administering to a mammal in need thereof a therapeutically effective amount of a composition of claim 15.

17. A method for treating cancer in which the ras gene is activated which comprises administering to a mammal in need thereof a therapeutically effective amount of a composition of claim 15.

* * * * *

UNITED STATES PATENT AND TRADEMARK OFFICE
CERTIFICATE OF CORRECTION

PATENT NO. : 5,536,750

DATED : July 16, 1996

INVENTOR(S) : S. Jane deSolms and Samuel L. Graham

It is certified that error appears in the above-identified patent and that said Letters Patent is hereby corrected as shown below:

At Column 31, Claim 3, line 19 should read as follows:

a) a side chain of naturally occurring amino acids,

Signed and Sealed this--

Fifth Day of November, 1996

Attest:

BRUCE LEHMAN

*Attesting Officer*    *Commissioner of Patents and Trademarks*